(12) United States Patent
Nirasawa et al.

(10) Patent No.: US 8,663,908 B2
(45) Date of Patent: Mar. 4, 2014

(54) METHOD OF REMOVING ABNORMAL PRION PROTEIN FROM PLASMA OR ERYTHROCYTE PRODUCT

(75) Inventors: Hiromi Nirasawa, Tokyo (JP); Morikazu Miura, Tokyo (JP)

(73) Assignee: Asahi Kasei Medical Co., Ltd., Tokyo (JP)

( * ) Notice: Subject to any disclaimer, the term of this patent is extended or adjusted under 35 U.S.C. 154(b) by 726 days.

(21) Appl. No.: 12/373,081

(22) PCT Filed: Jul. 12, 2007

(86) PCT No.: PCT/JP2007/000755
§ 371 (c)(1),
(2), (4) Date: Dec. 13, 2010

(87) PCT Pub. No.: WO2008/007465
PCT Pub. Date: Jan. 17, 2008

(65) Prior Publication Data
US 2010/0062412 A1    Mar. 11, 2010

(30) Foreign Application Priority Data
Jul. 12, 2006  (JP) ................................. 2006-191895

(51) Int. Cl.
*A01N 1/02*  (2006.01)
*B01D 37/00*  (2006.01)
*C02F 1/44*  (2006.01)
*A61M 37/00*  (2006.01)

(52) U.S. Cl.
USPC ............... 435/2; 210/651; 210/767; 604/5.02

(58) Field of Classification Search
None
See application file for complete search history.

(56) References Cited

U.S. PATENT DOCUMENTS

| | | |
|---|---|---|
| 6,197,207 B1 | 3/2001 | Chapman et al. |
| 2004/0104165 A1 | 6/2004 | Oishi et al. |
| 2004/0253204 A1 | 12/2004 | Yagi et al. |
| 2005/0014127 A1 | 1/2005 | Onodera et al. |
| 2005/0014196 A1 | 1/2005 | Carbonell et al. |

FOREIGN PATENT DOCUMENTS

| | | |
|---|---|---|
| EP | 1 356 855 A1 | 10/2003 |
| EP | 1 473 310 A1 | 11/2004 |
| JP | 2001-276181 | 10/2001 |
| JP | 2003-190276 | 7/2003 |
| JP | 2006-95139 | 4/2006 |
| JP | 2006-522344 | 9/2006 |
| WO | 98/52627 A1 | 11/1998 |
| WO | WO/02/60557 | 8/2002 |
| WO | WO/03/011924 | 2/2003 |
| WO | WO/2004/090102 | 10/2004 |

OTHER PUBLICATIONS

European Search Report that issued with respect to European Patent App. No. 07790251.8, dated Jun. 2, 2010.
Guide to the Preparation, Use, and Quality assurance of Blood Components, 9th edition Red Cells (Council of Europe, 2003), Chapters 4-12, pp. 85-122.
G. Chazot, et al., New variant of Creutzfeldt-Jakob disease in a 26-year-old French man, The Lancet, 1996, p. 1181, 347.
R.G. Will, et al., A new variant of Creutzfeldt-Jakob disease in the UK, The Lancet, 1996, pp. 921-925, 347.
Azuma et al., "New Movement of Blood Program—Eight Strategies for the Sake of Safer Blood Products", Artifial Blood, vol. 13, No. 1, 2005, pp. 6-12.
Barclay et al., "Distribution of cell-associated prion protein in normal adult blood determined flow cytometry", British Journal of Haematology, vol. 107, 1999, pp. 804-814.

*Primary Examiner* — Sandra Saucier
(74) *Attorney, Agent, or Firm* — Greenblum & Berstein P.L.C.

(57) ABSTRACT

Provided are a method of conveniently and efficiently removing abnormal prion protein from a blood product and a method of removing leukocyte simultaneously with abnormal prion protein. The method of removing an abnormal prion protein from a blood product includes filtering the blood product through a filter filled with a carrier coated with a polymer, which is composed of three units including 20 mol % or more and 40 mol % or less of a unit originating from a hydrophobic polymerizable monomer, 5 mol % or more and 13 mol % or less of a unit originating from a polymerizable monomer containing a basic nitrogen-containing part, and a unit originating from a polymerizable monomer containing a protonic neutral hydrophilic part as the balance, and then recovering the filtered blood product.

17 Claims, 1 Drawing Sheet

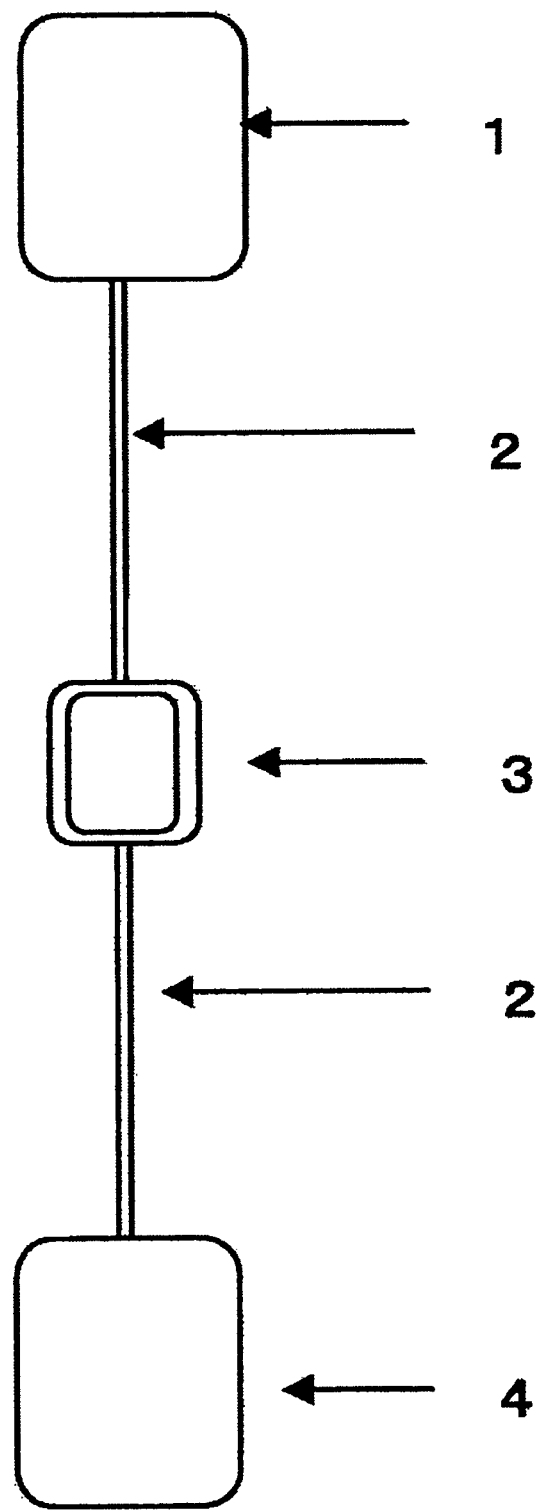

METHOD OF REMOVING ABNORMAL PRION PROTEIN FROM PLASMA OR ERYTHROCYTE PRODUCT

TECHNICAL FIELD

The present invention relates to a method of removing an abnormal prion protein from a blood product. More specifically, the present invention relates to a method of selectively removing an abnormal prion protein that may be present in a blood product such as a whole blood product, concentrated erythrocyte or concentrated platelet solution.

BACKGROUND ART

Transmissible spongiform encephalopathy (TSE) or prion disease causes fatal neurodegenerative diseases in humans and other mammals. Of those, scrapie in sheep and BSE in cattle are particularly widely known. The disease in humans includes sporadic Creutzfeldt-Jakob disease (sCJD), iatrogenic Creutzfeldt-Jakob disease, Gerstmann-Straeussler-Scheinker (GSS) syndrome, fatal familial insomnia (FFI), and Kuru. The prion disease may occur by the conformational change of a natural normal prion to a variant abnormal prion (a variant prion protein that may cause the prion disease), which infects humans and other mammals. The variant prion protein has a β-sheet-rich structure compared with the normal prion protein, so the variant prion protein has high hydrophobicity, easily forms a multimer, and has resistance to protease K.

In recent years, some reports have revealed that variant CJD occurred mainly in the United Kingdom is caused by consumption of beef from a cow infected with BSE (Non-Patent Documents 1 and 2). There has been suggested that variant CJD may be transmitted by consumption of beef and transmitted from human to human by transfusion of a blood product or by transmitting a variant prion protein present in a graft of a tissue. Under the circumstances, in 2004, two cases were reported where recipients transfused with blood of a donor who developed variant CJD after blood donation were infected with the variant CJD, and in 2006, the third case was reported, so there is a very strong possibility that transmission of the variant CJD may occur by transfusion. There is quite a lot of humans who are infected with variant CJD but do not develop the disease, and blood products derived from such humans may spread the infection. Therefore, a method of removing an abnormal prion protein from a blood product is required.

In the field of a blood transfusion, a so-called leukocyte-removed blood transfusion has been spread, by which a blood product is transfused after the leukocyte contained in the blood product is removed. This is because it has been clarified that side effects such as headache, nausea, chill, and non-hemolytic febrile reaction which accompany the blood transfusion; grave side effects such as alloantigen sensitization, posttransfusion graft-versus-host disease (GVHD), and virus infection which seriously affect the recipient are caused mainly by the leukocyte mixed in the blood product used in the blood transfusion. A filter method has such advantages as excellent leukocyte-removing capability, simple operation, and low cost, so the filtering method has been widely used as a method of removing leukocytes from a blood product. In processing a blood product, blood has been generally filtered at the blood center, in recent years, before storage to carry out thorough quality control of a leukocyte-removed blood product by the filter method, that is, by using a leukocyte removal filter. In general, in the case where blood is filtered using a leukocyte removal filter at the blood center, a blood bag containing a blood product to be filtered is placed at a position higher than a recovery bag for the post-filtration blood product the by 70 cm to 150 cm, and the blood product is filtered based on action of gravity.

As sets for preparing a leukocyte-removed blood product, two sets (SCD-type and inline-type sets) are widely used. In the SCD-type set, a bag containing a blood product intended for removing leukocytes is aseptically connected to the set to remove leukocytes. Accordingly, only the leukocyte removal filter and the blood bag for recovering a blood product after filtration are connected. In the inline-type set, the process from blood recovery from a donor to preparation of a blood product is performed in an integrated system, so the blood bag generally contains a preservative solution or anticoagulant. To sterilize the SCD-type set, radiation sterilization is generally employed because of low cost. However, the radiation sterilization may cause decomposition of the preservative solution and anticoagulant, thus autoclave sterilization is generally employed for the inline-type set.

Degree of hemolysis is among the indices of the quality of a blood product containing erythrocytes. To supply a high-quality leukocyte-removed blood product containing erythrocytes, the Hemolysis Level should be less than 0.8% (Non-Patent Document 3).

From a viewpoint of operativity at the blood center, cost, and loss of a blood product, the method of removing an abnormal prion protein from a blood product is preferably a method of removing an abnormal prion protein and leukocyte simultaneously.

Patent Document 1 discloses a polymer for coating a leukocyte removal filter material including a unit originating from a hydrophobic polymerizable monomer, a unit originating from a polymerizable monomer containing a basic nitrogen-containing part, and a unit originating from a polymerizable monomer containing a protonic neutral hydrophilic part as a material having high leukocyte-removing capability, but does not disclose and suggest removal of an abnormal prion protein. Filtration of leukocyte-removed blood before storage includes, in many cases, both room-temperature filtration in which blood is filtered at room temperature within one day of collection of the blood and low-temperature filtration in which blood is filtered after blood storage in a refrigerator for about 1 to 3 days. In the case of the room-temperature filtration, more leukocytes leak than refrigerated blood although the filtration time is short, while in the case of the low-temperature filtration, the filtration time is long, and leakage of leukocytes may be relatively prevented. However, in Patent Document 1, no study has been made on the filtration time in the low-temperature filtration.

Patent Document 2 discloses a method of forming a complex of a prion protein in a biological fluid and a polymer matrix having a hydrophilic, hydrophobic, or amphiphilic functional group or a prion-binding substance including alumina or silica. However, the complex cannot remove leukocytes although the functional group is linked to a resin in examples, and it is necessary to use a leukocyte removal filter in actual use at the blood center. If removal of leukocytes and removal of abnormal prion proteins are performed separately, loss of a blood product, labor at the blood center, and cost may increase. In addition, alumina and silica are known to induce activation of a clotting system and show high nonselective adsorption for proteins, and hence the substances are not suitable for a blood product.

Patent Document 3 discloses a method of removing prions from an arbitrary liquid sample by using an apparatus such as a flow-through column and spherical polymer beads, the surfaces of which are coated with a prion complexing agent such as a metal salt (such as sodium) of phosphotungstic acid. However, it is necessary to expose the sample to the complexing agent for enough time to form complexes of the prion complexing agent and substantially all abnormal prion proteins in the sample. For example, the sample is incubated at about 30° C. to 45° C. (preferably 37° C.) for about 1 hour to 16 hours. However, the temperature of 37° C. is not suitable as a temperature for storing a blood product, and in a conventional method of using a leukocyte removal filter, room-temperature or low-temperature filtration is generally employed. In addition, in such method, filtration is performed based on action of gravity, so the method is not suitable for removal of abnormal prion proteins or leukocytes from a blood product. Patent Document 4 discloses a method of forming a complex of a prion protein and a polymer matrix having a hydrophilic, hydrophobic, or amphiphilic functional group for removing or detecting a prion, or a prion-binding substance including alumina or silica. However, the prion-binding substance used in examples cannot remove leukocytes, and if removal of leukocytes and removal of abnormal prion proteins are performed separately, there are problems that loss of a blood product, labor at the blood center, and cost may increase. In addition, alumina and silica are known to induce activation of a clotting system and have high nonselective adsorbability for proteins, and hence the substances are not suitable for a blood product.

Therefore, in order to remove an abnormal prion protein from a blood product, a method of efficiently and easily removing the abnormal prion protein is required, and the method is further desired to remove the abnormal prion protein and leukocyte simultaneously.

[Non-Patent Document 1] G. Chazot, et al., (1996) Lancet 347:1181
[Non-Patent Document 2] R. G. Will, et al., (1996) Lancet 347:921-25
[Non-Patent Document 3] Guide to the preparation, use and quality assurance of blood components 9th edition/Council of Europe Publishing
[Patent Document 1] WO 03/011924
[Patent Document 2] US 2005/0014196 A
[Patent Document 3] JP 2002-539081 A
[Patent Document 4] JP 2006-522344 A

DISCLOSURE OF THE INVENTION

Problems to be Solved by the Invention

In view of the above-mentioned problems of conventional technologies, an object of the present invention is to provide a method of easily and efficiently removing an abnormal prion protein from a blood product and a method of simultaneously removing an abnormal prion protein and leukocyte.

Means for Solving the Problems

The inventors of the present invention have made extensive studies, with the result that the inventors have found out that an abnormal prion protein can be very easily and efficiently removed from a blood product by a filter coated with a terpolymer including a hydrophobic polymerizable monomer, a polymerizable monomer containing a basic nitrogen-containing part, and a polymerizable monomer containing a protonic neutral hydrophilic part (not a polymer including any one of the monomers), thus completed the present invention. That is, the present invention relates to:

(1) a method of removing an abnormal prion protein from a blood product, characterized by including: filtering a blood product through a filter packed with a carrier coated with a polymer, which is formed of three units including 20 mol % or more and 40 mol % or less of a unit originating from a hydrophobic polymerizable monomer, 5 mol % or more and 13 mol % or less of a unit originating from a polymerizable monomer containing a basic nitrogen-containing part, and a unit originating from a polymerizable monomer containing a protonic neutral hydrophilic part as the balance; and recovering the filtered blood product;

(2) a method of removing an abnormal prion protein from a blood product according to the above-mentioned item (1), characterized in that the blood product is a whole blood product, and the filter is subjected to radiation sterilization and then autoclave sterilization;

(3) a method of removing an abnormal prion protein from a blood product according to the above-mentioned item (2), characterized in that the radiation is γ-rays or electron beams;

(4) a method of removing an abnormal prion protein from a blood product according to any one of the above-mentioned items (1) to (3), characterized in that the polymer is a vinyl-type polymer;

(5) a method of removing an abnormal prion protein from a blood product according to any one of the above-mentioned items (1) to (4), characterized in that the hydrophobic polymerizable monomer, polymerizable monomer containing a basic nitrogen-containing part, and polymerizable monomer containing a protonic neutral hydrophilic part are acrylic acid derivatives and/or methacrylic acid derivatives;

(6) a method of removing an abnormal prion protein from a blood product according to any one of the above-mentioned items (1) to (5), characterized in that the basic nitrogen-containing part is a tertiary amino group;

(7) a method of removing an abnormal prion protein from a blood product according to any one of the above-mentioned items (1) to (6), characterized in that the protonic neutral hydrophilic part is a hydroxyl group;

(8) a method of removing an abnormal prion protein from a blood product according to any one of the above-mentioned items (1) to (7), characterized in that the filter is a leukocyte removal filter;

(9) a method of removing an abnormal prion protein from a blood product according to the above-mentioned item (8), characterized in that the carrier coated with the polymer is a fibrous medium or a sponge-like structural material;

(10) a method of removing an abnormal prion protein from a blood product according to the above-mentioned item (8) or (9), characterized in that a specific surface area of the carrier coated with the polymer is 1.0 $m^2/g$ or more and 5.0 $m^2/g$ or less;

(11) a method of removing an abnormal prion protein from a blood product according to any one of the above-mentioned items (8) to (10), characterized in that an average pore diameter of the carrier coated with the polymer is 1 μm or more and 60 μm or less;

(12) a method of removing an abnormal prion protein from a blood product according to any one of the above-mentioned items (8) to (11), characterized in that a filling density of the carrier coated with the polymer is 0.1 $g/cm^3$ or more and 0.5 $g/cm^3$ or less;

(13) a method of removing an abnormal prion protein from a blood product according to any one of the above-mentioned items (8) to (12), characterized in that porosity of the carrier coated with the polymer is 60% or more and 90% or less;

(14) a method of removing an abnormal prion protein from a blood product according to any one of the above-mentioned items (8) to (13), characterized in that the carrier coated with the polymer is a nonwoven fabric; and

(15) a method of removing an abnormal prion protein from a blood product according to the above-mentioned item (14), characterized in that a fiber diameter of the nonwoven fabric is 0.3 μm or more and 3.0 μm or less.

Effect of the Invention

According to the present invention, it is possible to easily and efficiently remove an abnormal prion protein from a blood product and to simultaneously remove an abnormal prion protein and leukocyte. In addition, the method of the present invention can be used to produce a high-quality blood product that has high flowability and contains less hemolyzed cells.

BRIEF DESCRIPTION OF THE DRAWING

FIG. 1 is a schematic view illustrating a system for carrying out the present invention.

DESCRIPTION OF REFERENCE NUMERALS

1: bag of blood product
2: line
3: filter
4: bag for recovering blood product after filtration

BEST MODE FOR CARRYING OUT THE INVENTION

Hereinafter, the present invention is described in more detail. The term "polymer" in the present invention means polymer(s) including a unit originating from a hydrophobic polymerizable monomer, a unit originating from a polymerizable monomer containing a basic nitrogen-containing part, and a unit originating from a polymerizable monomer containing a protonic neutral hydrophilic part.

The term "unit" in the present invention means a minimum repeating unit originating from each polymerizable monomer in a polymer molecule. For example, in the case of the addition polymerization of a polymerizable monomer of vinyl compound with the formula $CH_2=CXY$ (X: H or a substituent other than H, Y: a substituent other than X) by simply opening the double bond, the minimum repeating unit is —($CH_2$—CXY)—. In the case where the polymer is synthesized by polycondensation from a polymer precursor of the formula A-(R)—B, (R: a part not releasable by polymerization, A and B: releasable parts during the polymerization reaction), —(R)— can be given as the minimum repeating unit when A and B are released and polymerized.

Examples of the hydrophobic polymerizable monomer, specifically from the viewpoint of ease of availability and handling, include: styrene; methylstyrene; acrylates and methacrylates such as methyl acrylate, methyl methacrylate, ethyl acrylate, ethyl methacrylate, butyl acrylate, butyl methacrylate, phenyl acrylate, phenyl methacrylate, ethylhexyl acrylate, ethylhexyl methacrylate, trichloroethyl acrylate, and trichloroethyl methacrylate; alkenes such as pentene, hexene, heptene, and octene; organic silicon compounds such as silicone and siloxane; and organic fluorine polymerizable monomers having at least one hydrogen atom of ethylene substituted with a fluorine atom. However, the hydrophobic polymerizable monomer is not limited to the above substances. Of these, from the viewpoint of easy availability and easy handling, monomers having a vinyl group as a polymerizable part that can produce a vinyl-type polymer by addition polymerization (vinyl polymerization) are preferable. Moreover, preferable hydrophobic polymerizable monomers are acrylic acid derivatives and methacrylic acid derivatives. Acrylates and methacrylates are most preferable hydrophobic polymerizable monomers.

Materials having a basic nitrogen-containing functional group have positive charges on the surface in a physiological fluid, which provides the effect of enhancing abnormal prion protein-removing capability. The term "polymerizable monomer containing a basic nitrogen-containing part" in the present invention means a polymerizable monomer which has a basic nitrogen-containing part to be described below. A primary amino group, a secondary amino group, a tertiary amino group, a quaternary amino group, a nitrogen-containing aromatic group, such as a pyridyl group and an imidazoyl group, and the like can be given as the basic nitrogen-containing part. The tertiary amino group is particularly preferred as the basic nitrogen-containing part. The polymerizable monomer containing a basic nitrogen-containing part include, from the viewpoint of easy availability and easy handling, vinyl derivatives of a nitrogen-containing aromatic compound such as vinylamine, 2-vinylpyridine, 4-vinylpyridine, 2-methyl-5-vinylpyridine, 4-vinylimidazole, N-vinyl-2-ethylimidazole, and N-vinyl-2-methylimidazole; acrylates and methacrylates such as dimethylaminoethyl acrylate, dimethylaminoethyl methacrylate, diethylaminoethyl acrylate, diethylaminoethyl methacrylate, 3-dimethylamino-2-hydroxypropyl acrylate, and 3-dimethylamino-2-hydroxypropyl methacrylate; acrylic acid amide and methacrylic acid amide derivatives such as N,N-dimethylaminoethyl acrylic acid amide, N-dimethylaminoethyl methacrylic acid amid, N,N-diethylaminoethyl acrylic acid amid, N,N-diethylaminoethyl methacrylic acid amid, and N,N-dimethylaminopropyl acrylic acid amid; styrene derivatives such as p-dimethylaminomethylstyrene and p-diethylaminoethylstyrene; and derivatives such as quaternary ammonium salts prepared by reacting the polymerizable monomer with an alkyl halide group. However, the polymerizable monomer containing a basic nitrogen-containing part is not limited to the substances. Of these, from the viewpoint of easy availability and easy handling, monomers having a vinyl group as a polymerizable part that can produce a vinyl-type polymer by addition polymerization (vinyl polymerization) are preferable. Acrylic acid derivatives and methacrylic acid derivatives are preferable for the polymerizable monomer containing a basic nitrogen-containing part. Acrylates and methacrylates are more preferable for the polymerizable monomer containing a basic nitrogen-containing part. Of those, dimethylaminoethyl acrylate, dimethylaminoethyl methacrylate, diethylaminoethyl acrylate, and diethylaminoethyl methacrylate are particularly preferable.

The term "polymerizable monomer containing a protonic neutral hydrophilic part" in the present invention means a monomer of which the non-polymerizable part dissociates to release protons ($H^+$), and the monomer does not exhibit extreme acidity or extreme basicity as a carboxylic acid or a basic amino group do so. The polymerizable monomer containing a protonic neutral hydrophilic part exhibits higher hydrophilic properties as compared with a monomer having a nonprotonic neutral hydrophilic part and excels in priming properties and blood channeling preventive properties of the blood product. Examples of the protonic neutral hydrophilic part include a hydroxyl group, an aldehyde group having a proton in the α-position and an amide group having a proton in the α-position, and a 1,3-dicarbonyl group. As the non-polymerizable protonic neutral hydrophilic part, a hydroxyl group is particularly preferable. Examples of polymerizable monomers containing a protonic neutral hydrophilic part include 2-hydroxyethyl methacrylate, hydroxypropyl methacrylate, hydroxybutyl acrylate, acrylamide, and methacrylamide. However, the polymerizable monomers containing a protonic neutral hydrophilic part are not limited to the above substances. Of these, from the viewpoint of easy availability and easy handling, monomers having a vinyl group as a polymerizable part that can produce a vinyl-type polymer by addition polymerization (vinyl polymerization) are preferable. Of those, as polymerizable monomers containing a protonic neutral hydrophilic part, acrylic acid derivatives and methacrylic acid derivatives are preferable. Acrylates and methacrylates are the most preferable for the polymerizable monomers containing a protonic neutral hydrophilic part. The term "vinyl-type polymer" in the present invention means a vinyl-type polymer in a broad sense having noncyclic main chain. Specific examples include α-substituted polyacrylic acid and derivatives thereof, polyvinyl ether, polyvinyl alcohol, polyvinyl ester, polystyrene, and derivatives thereof, as well as copolymers including those polymers, as described in "J Brandrup; E. H. Immergut. 1989. "Polymer Hand book Third Edition" A Willey-interscience Publication, pVII-5 to VII-18".

To remove an abnormal prion protein in a blood product containing a plasma component, it is necessary to use the above-mentioned polymer containing three units including a unit originating from a hydrophobic polymerizable monomer, a unit originating from a polymerizable monomer containing a basic nitrogen-containing part, and a unit originating from a polymerizable monomer containing a protonic neutral hydrophilic part. Even if a polymer including only one of the units is used, it is impossible to remove an abnormal prion protein at a high level and impossible to provide high abnormal prion protein-removing capability particularly from a blood product containing a plasma component.

The abnormal prion protein has three distinct binding regions that bind to positively-charged functional groups, negatively-charged functional groups, and hydrophobic functional groups. Meanwhile, the isoelectric point of the abnormal prion protein was reported to be pH 4.6, and pH of a blood product is in the range of about 5 to 7.5, so the abnormal prion protein in a blood product is negatively charged. Therefore, the monomer containing a basic nitrogen-containing part and hydrophobic polymerizable monomer can remove the abnormal prion protein from the blood product at a high level. In addition, it is known that a contact between a material having negative charges and a blood product may cause production of bradykinin that induces anaphylaxis such as decrease in blood pressure, face flush, conjunctival hyperemia, contraction of smooth muscle, or pain generation, and such a polymer having negative charges is not suitable to coat the surface of a carrier to be used for filtration of the blood product.

On the other hand, filtration of the blood product using a filter is required to provide a blood product having the same quality as a blood product obtained by filtration using a conventional leukocyte removal filter. The protonic neutral hydrophilic part of the polymer is an essential part for securing wettability necessary for spreading the blood product to the entire filter, in particular, for performing smooth "priming" that is a procedure of filling the filter with the blood product at the initial stage of filtration. If the compositions of the monomer containing a basic nitrogen-containing part and hydrophobic polymerizable monomer in the polymer exceed certain levels, reduction in quality is caused, resulting in hemolysis or prolonged filtration time. Therefore, to produce a blood product where an abnormal prion protein has been removed at a high level, it is necessary to adjust the composition of the hydrophobic polymerizable monomer, polymerizable monomer containing a basic nitrogen-containing part, and polymerizable monomer containing a protonic neutral hydrophilic part in appropriate ranges.

The term "hydrophobic polymerizable monomer" in the present invention means a polymerizable monomer having very low affinity for water and having water solubility of 12 (g/100 g of water) or less at 20° C., and means a monomer containing neither a basic nitrogen-containing part nor a protonic neutral hydrophilic part in its molecule. If the solubility is more than 12 (g/100 g of water), the high abnormal prion protein-removing capability available in the present invention may not be obtained. More preferable range of solubility is 2 (g/100 g of water) or less. The solubility can be determined by a known method, such as a dew point method, thermal analysis, electric method comprising measuring the electromotive force or electric conductivity of the solution, gas chromatography analysis, and tracer method, in the case where the polymerizable monomer is a solid. In the case where the polymerizable monomer is a liquid, the solubility can be determined by the same methods as applied to a solid polymerizable monomer, and in addition, by a known method such as a capacitance method, light scattering method, or vapor pressure method, all of which are known in the art. As a simpler method, when the polymerizable monomer has a boiling point sufficiently higher than the boiling point of water, a method, in which water is vaporized from a saturated aqueous solution of the polymerizable monomer and the weight of the residue is measured, can be used.

To achieve higher abnormal prion protein-removing capability and leukocyte-removing capability, the polymer preferably includes the above-mentioned monomers at the following concentrations (mol percentage): the hydrophobic polymerizable monomer, 20 mol % or more and 40 mol % or less; the polymerizable monomer containing a basic nitrogen-containing part, 5 mol % or more and 13 mol % or less; the polymerizable monomer containing a protonic neutral hydrophilic part, a concentration calculated by subtracting the sum of the concentration (mol %) of the hydrophobic polymerizable monomer in the polymer and the concentration (mol %) of the polymerizable monomer containing a basic nitrogen-containing part from 100 mol %. If the concentration of the hydrophobic polymerizable monomer in the polymer is less than 20 mol %, or if the concentration of the polymerizable monomer containing a basic nitrogen-containing part is less than 5 mol %, undesirably the abnormal prion protein-removing capability may not be improved. If the concentration of the hydrophobic polymerizable monomer in the polymer exceeds 40 mol %, undesirably, wettability for a blood product stored in a refrigerator may be impaired, resulting in a decrease in a filtration rate of the blood product when filtering the blood product using a filter filled with a carrier coated with a polymer of the present invention. If the concentration of the polymerizable monomer containing a basic nitrogen-containing part in the polymer exceeds 13 mol %, hemolysis may undesirably occur in the blood product stored in a refrigerator. To achieve further higher abnormal prion protein-removing capability and leukocyte-removing capability, the polymer preferably includes the above-mentioned monomers at the following concentrations (mol percentage): the hydrophobic polymerizable monomer, 25 mol % or more and 35 mol % or less; the polymerizable monomer containing a basic nitrogen-containing part, 7 mol % or more and 12 mol % or less; the polymerizable monomer containing a protonic neutral hydrophilic part, a concentration calculated by subtracting the sum of the concentration (mol %) of the hydrophobic polymerizable monomer in the polymer and the concentration (mol %) of the polymerizable monomer containing a basic nitrogen-containing part from 100 mol %. Most preferably, the polymer includes the hydrophobic polymerizable monomer at a concentration of 27 mol % or more and 33 mol % or less, the polymerizable monomer containing a basic nitrogen-containing part at a copolymerization composition of 8 mol % or more and 11 mol % or less, and the polymerizable monomer containing a protonic neutral hydrophilic part as the balance.

The monomer composition in the polymers can be determined according to a common physicochemical technique. Examples of the physicochemical technique for determining the copolymerization compositions include known methods such as the nuclear magnetic resonance spectroscopy (NMR, -1H, -13C) and the pyrolysis GC/MS method. It can also be determined if the polymerization is carried out as intended with the charged monomer composition or if there are lot-to-lot variation. It is also possible to dissolve and extract the polymer coated on a carrier by using a solvent for the polymer and possible to analyze the monomer composition in the extracted polymer in the same manner as described above. It is also possible to apply a method of dissolving the carrier and the polymer present on the surface in a deuterated solvent and determining the composition by nuclear magnetic resonance spectroscopy (NMR, -1H, -13C) as a method to determine the copolymerization composition. The molecular weight of the polymer can be measured by the known gel permeation chromatography. The weight average molecular weight (Mw) is in the range of preferably 50,000 or more and 3,000,000 or less, more preferably 100,000 or more and 2,000,000 or less, and most preferably 150,000 or more and 1,500,000 or less. If the weight average molecular weight (Mw) is less than 50,000, elution of the polymer into the blood product may undesirably occur during an abnormal prion protein and leukocyte removal process using a blood product. If the weight average molecular weight (Mw) is more than 3,000,000, undesirably, solubility of the polymer in the solvent used for coating decreases. In addition, there may be the case where the polymer cannot be produced in a stable manner upon polymerizing. The polymer may be either a random copolymer or a block copolymer. The random polymer is, however, more preferable because the block copolymer may have a tendency of decreasing the solubility in a solvent when used for coating and may have a tendency of impairing uniformity of coat due to micelle formation in the solution. The polymer may be either a linear polymer or a branched polymer. The linear polymer chain is, however, more preferable because the branched polymer chain may have a tendency of decreasing the solubility in a solvent when used for coating and may have a tendency of impairing coating uniformity due to micelle formation in the solution. A common polymerization method can be employed for synthesizing the polymer. Addition polymerization (vinyl polymerization) which is a chain reaction; isomerization polymerization; and elimination reaction, polyaddition, polycondensation, addition polycondensation, and the like which are consecutive reactions may be employed. Radicals or ions can be used as chain carriers in producing the polymer. As the type of polymerization, solution polymerization, mass polymerization, deposition polymerization, emulsion polymerization and the like can be referred as examples. Of these, the solution polymerization is preferable.

An example of the polymerization method is given below. Ethanol is used as a polymerization solvent, and an ethanol solution in which monomers and a diazo-type initiator have been dissolved is added dropwise to let the reaction occur, while the solution is stirring at a constant temperature equal to or less than the boiling point of ethanol in a nitrogen atmosphere. A stabilizer or the like may be added as appropriate. The reaction yield is measured and confirmed by using a known method such as gas chromatography. The reaction mixture may be purified by a common chemical purification method to remove impurities such as low molecular weight components and the unreacted materials which are contained in the polymer or the reaction solution containing the polymer and feared to be eluted during treatment of a product. As the purification method, a method including pouring the reaction mixture in a solvent that dissolves the impurities, but does not dissolve the polymer, to separate the precipitate by filtration or decantation can be given. Alternatively, a method that, as required, the precipitate is washed with a solvent with solubility slightly higher than that of the precipitation solvent (a mixture of the precipitation solvent and the solvent, for example) and the precipitate is dried under reduced pressure until the weight of the precipitate becomes constant to obtain a solid polymer can be given.

There are no specific limitations to the type of the carrier as much as the material has pores through which the blood can be filtered. Among the various conformations of the carrier that can be used, fibrous media such as natural fibers, glass fibers, knit, fabric, nonwoven fabric, porous membrane, and a sponge-like structural material having a three-dimensional network of continuous pores are particularly preferable. Various carriers such as organic polymer materials, inorganic polymer materials, and metals can be used without any specific limitations as long as blood cells are not easily impaired. Of those, the organic polymer materials are preferable materials due to their excellent processability such as cutting. For example, polyester, polyolefin, polyacrylonitrile, polyamide, polystyrene, polymethylmethacrylate, polyvinyl fluoride, polyurethane, polyvinyl alcohol, polyvinyl acetal, polysulfone, poly vinylidene fluoride, polytrifluorochlorovinyl, vinylidene fluoride-tetrafluoroethylene copolymer, polyethersulfone, polyacrylate, butadiene-acrylonitrile copolymer, polyether-polyamide block copolymer, ethylene-vinyl alcohol copolymer, cellulose, and cellulose acetate. However, the carrier of the present invention is not limited to the above-mentioned examples. Polyester and polyolefin are preferable, and polyester is particularly preferable.

The term "carrier coated with a polymer" in the present invention means a carrier obtained by fixing the polymer on the surface of the carrier in such a manner that the polymer is not easily eluted into the product during processed. As the method for fixing the polymer to the surface of the carrier, either a chemical method of using covalent bonding or a physicochemical method using noncovalent bonding may be employed. The amount of the polymer is preferably 0.6 $mg/m^2$ or more and 83 $mg/m^2$ or less. If the amount of the polymer is less than 0.6 $mg/m^2$ per unit area in the entire surface area of the carrier, undesirably, the abnormal prion protein-removing capability and leukocyte-removing capability tends to decrease; if the amount exceeds 83 $mg/m^2$, undesirably, the performance of the filter may fluctuate due to uneven coating. A more preferable amount of the polymer is 5 $mg/m^2$ or more and 50 $mg/m^2$ or less per unit area in the entire surface area of the carrier, with a particularly preferable amount being 10 $mg/m^2$ or more and 40 $mg/m^2$ or less. The amount of the polymer on the surface of the carrier can be determined according to a common physicochemical technique. As the method of measuring the abundance of the polymer on the surface of the carrier, a method of dissolving the coated carrier and the polymer present on the surface in a deuterated solvent and determining the amount by nuclear magnetic resonance method (NMR, -1H, -13C) can be given.

In the present invention, a carrier coated with a polymer is referred to as "coated carrier" in some cases.

As the method of coating the polymer on the carrier in the present invention, known methods such as a method of fixing the above-mentioned polymerizable monomers or the polymer on the carrier by chemical covalent bonding (e.g. grafting), a method of fixing by a physicochemical noncovalent bonding (ionic bond, Van der Waals force, etc.) (e.g., coating), and a method of embedding the polymer can be given. More specifically, a method of directly grafting the polymerizable monomers or the polymer on the surface of the carrier by graft polymerization method such as radiation grafting or plasma grafting or a method of coating a polymer onto the surface of a carrier by impregnating the carrier with a polymer solution or by applying on a roll and transcribing the polymer to the surface of the carrier is preferable in view of a comparatively easy manufacturing process that can produce products with excellent performance in a stable manner. Various methods can be used for coating the polymer of the present invention onto the carrier without any specific limitations asmuch as the surface of the carrier can be coated with a certain degree of uniformity without unduly clogging the pores in the carrier. Examples of the method of coating the polymer onto the carrier include, but are not limited to, a method of impregnating the carrier with a polymer solution, a method of spraying the polymer solution to carrier, and a method of applying or transcribing the polymer solution to the carrier using a photogravure roll. Of these methods, the method of impregnating the carrier with a polymer solution and squeezing the carrier and the method of applying or transcribing the polymer solution to the carrier using a photogravure roll are preferable due to the excellent continuous productivity and a low cost. The types of solvents which may be used as the solvents that dissolve the polymer are not particularly limited as long as they are those which do not dissolve the carrier. Examples thereof include: solutions containing water and inorganic salts; alcohols such as methanol, ethanol, propanol, and butanol; ketones such as acetone and methylethyl ketone; esters such as methyl acetate and ethyl acetate; hydrocarbons such as benzene and cyclohexane; halogenated hydrocarbons such as chloroform and dichloromethane; sulfur-containing solvents such as dimethylsulfoxide; amides such as dimethylformamide and dimethylacetamide; and mixtures of plural kinds of the above-mentioned solvents in the range in which they are soluble. However, the solvents which may be used as the solvents that dissolve the polymer of the present invention are not particularly limited to the above-mentioned examples. To dry the polymer solution after coating, a method including removing excess solvent by mechanical compression or by injecting gas such as air or nitrogen, and leaving the coated carrier in dry air or under reduced pressure at atmospheric temperature or with heating can be employed. To increase adhesion of the polymer of the present invention to the carrier, the surface of the carrier may be treated with a suitable agent such as an acid or alkali or may be irradiated with plasma before coating. Adhesion of the polymer to the carrier may be further increased by a heat treatment after coating with the polymer or by post-treatment of irradiating the coated surface with radiation such as γ-rays or electron beams. The coating operation may be carried out either during manufacturing the carrier or after manufacturing the carrier.

The physical structure of the coated carrier is known to greatly contribute to removing an abnormal prion protein and leukocyte. To improve the abnormal prion protein- and leukocyte-removing capability, selection of the coated carrier is also an important factor. With regard to a physical structure of the coated carrier, the specific surface area is $1.0 \, m^2/g$ or more and $5.0 \, m^2/g$ or less, preferably $1.1 \, m^2/g$ or more and $3.0 \, m^2/g$ or less, and more preferably $1.3 \, m^2/g$ or more and $2.0 \, m^2/g$ or less. If the specific surface area of the coated carrier is less than $1.0 \, m^2/g$, it is difficult to remove leukocytes at a high efficiency. If the specific surface area of the coated carrier is exceeds $5.0 \, m^2/g$, it is impossible to steadily produce a coated carrier. In processing a product using a blood filter in practice, two or more coated carriers with a different specific surface area are preferably arranged in such a manner that the specific surface area of the carrier increases toward the outlet-port side.

With regard to a physical structure of the coated carrier, the porosity is preferably 65% or more and 90% or less, more preferably 75% or more and 88% or less. If the porosity is less than 65%, the filtration rate of blood is decreased, a longer time for removing an abnormal prion protein and leukocyte is required. Meanwhile, if the porosity is exceeds 90%, the number of intersecting sites between fibers, which may adhere to abnormal prion proteins and leukocytes, is small, resulting in low abnormal prion protein-removing capability and leukocyte-removing capability. When a fibrous medium such as a nonwoven fabric as the coated carrier is used, the average fiber diameter is 0.3 μm or more and 3.0 μm or less, preferably 0.5 μm or more and 2.5 μm or less, more preferably 1 μm or more and 2 μm or less. In processing a blood product using a blood filter in practice, two or more coated carriers with different average fiber diameters are preferably arranged so that the average fiber diameter of the carriers decreases toward the outlet-port side. In processing a blood product using a blood filter in practice, a carrier with an average fiber diameter of 10 μm or more and 40 μM or less may be optionally arranged on the inlet-port side of the coated carrier with a major objective of removing fine aggregates.

The average pore diameter is a value (mean flow pore size: MFP) obtained by measurement for a sample of about 50 mg using Coulter R porometer manufactured by Coulter Electronics. The average pore diameter is 1 μm or more and 60 μm or less, preferably 1 μm or more and 30 μm or less, more preferably 1 μm or more and 20 μm or less. If the average pore diameter is less than 1 μm, undesirably, the whole blood product is hard to flow, while if the average pore diameter exceeds 60 μm, undesirably, the leukocyte-removing capability may be compromised. In processing a blood product using a blood filter in practice, two or more coated carriers with different average pore diameters are preferably arranged so that the average pore diameter of the carriers decreases toward the outlet-port side. In processing a blood product using a blood filter in practice, a carrier with average pore diameters of 50 μm or more and 200 μm or less may be optionally arranged on the inlet-port side of the filter material with a major objective of removing fine aggregates.

In processing a product using a blood filter in practice, a carrier with an average pore diameter of 50 μm or more and 200 μm or less may be optionally arranged on the outlet-port side of the coated carrier with a major objective of preventing a distorted flow.

When the fibrous medium is filled in a container for removing abnormal prion proteins and leukocytes, the filling density is preferably $0.1 \, g/cm^3$ or more and $0.5 \, g/cm^3$ or less, and more preferably $0.1 \, g/cm^3$ or more and $0.3 \, g/cm^3$ or less. A method of measuring the filling density is described by way of an example. A nonwoven fabric to be filled in is cut into pieces with a filling size ($cm^2$), and weights (g) of the pieces are measured. The density can be determined from the distance (cm) of the material compressed in the actual container.

If the average fiber diameter is either less than 0.3 μm, the average pore diameter is less than 1 μm, or the filling density is more than 0.5 g/cm$^3$, the filter may be clogged with blood cells or the pressure loss may be increased. If the average fiber diameter is more than 3.0 μm, the average pore diameter is more than 60 μm, or the filling density is less than 0.1 g/cm$^3$, undesirably, the abnormal prion protein and leukocyte-removing capability may be decreased.

A porous membrane or a sponge-like structural material having a three-dimensional network of continuous pores used as a coated carrier preferably has an average pore diameter of 1 μm or more and 60 μm or less, preferably 5 μm or more and 50 μm or less, more preferably 10 μm or more and 40 μm or less. If the average pore diameter is less than 1 μm, the filter may be clogged with blood cells or the pressure loss may be undesirably caused. If the average pore diameter is more than 60 μm, the leukocyte-removing capability undesirably declines.

The term "abnormal prion protein" in the present invention means a variant abnormal prion protein that is known to cause a disease called spongiform encephalopathy in human and animals. The abnormal prion protein has the same amino acid sequence as that of a normal prion but has an altered β-sheet-rich conformation and is resistant to digestion with protease K. Abnormal prion proteins may infect animals to cause scrapie that is an infectious degenerative disease of the nervous system of sheep and goat and BSE in cattle. In the case of human, abnormal prion proteins may cause sporadic Creutzfeldt-Jakob disease (sCJD), iatrogenic Creutzfeldt-Jakob disease, Gerstmann-Straeussler-Scheinker (GSS) syndrome, fatal familial insomnia (FFI), Kuru, and variant CJD known to be transmitted through BSE meat. The abnormal prion proteins to be used in the present invention include all types of abnormal prion proteins that may cause any one or all of the above-mentioned diseases in any animal, particularly in human and domestic animals. In fact, according to the report by Samuel Coker in Cambridge Healthtech Institut's $10^{th}$ Annual Transmissible Spongiform Encephalopathies—The Definitive American TSE Meeting—in March 2006, abnormal prion proteins derived from scrapie variant CJD and sporadic CJD are removed at the same degree using a filter (LAPRF, manufactured by Pall), and there is no significant difference in removal ratios. This suggests that the protein structures of the abnormal prion proteins relating to filter removing capability are almost the same even if the species of animals or diseases are different, and that the removal ratio of an abnormal prion protein derived from human can be estimated based on the removal ratio of an abnormal prion protein derived from an animal.

The term "filter" in the present invention means a product obtained by filling a container for a blood product having an inlet port and an outlet port with the coated carrier of the present invention, and there may be a carrier for capturing minute aggregates on the upstream side of the blood product or on the downstream side.

The container material may be either a hard resin or a flexible resin. In the case of the hard resin, examples may include a phenol resin, an acrylic resin, an epoxy resin, a formaldehyde resin, a urea resin, a silicon resin (silicone), an ABS resin, nylon, a hard polyurethane, polycarbonate, vinyl chloride, polyethylene, polypropylene, and polyester etc. In the case of the flexible resin, materials obtained by forming an inlet port and an outlet port of a blood product on sheets formed of a flexible synthetic resin, then welding the resultants at peripheral parts, or a cylindrical molded product having an inlet port and an outlet port of a blood product can be used. In the case where the material is adhered to the container with the coating carrier, those having similar thermal, electrical properties are preferred. Examples of appropriate materials include polyolefins such as soft polyvinyl chloride, polyurethane, ethylene-vinyl acetate copolymer, polyethylene and polypropylene, thermoplastic elastomers such as hydrogenated styrene-butadiene-styrene copolymer, styrene-isoprene-styrene copolymer or hydrogenated products thereof, and mixtures of the thermoplastic elastomer and a softening agent such as polyolefin or ethylene-ethyl acrylate, or the like. Of those, soft polyvinyl chloride, polyurethane, ethylene-vinyl acetate copolymer, polyolefin, and the thermoplastic elastomer containing thereof as the main component are more preferable, with soft polyvinyl chloride and polyolefin being particularly preferable.

There are no specific limitations to the type of the shape of the container as long as the container has a shape with an inlet port of a blood product and an outlet port of a blood product from which the abnormal prion protein and leukocyte are removed, but the shape preferably depends on the shape of the carrier. For example, in the case of using a carrier in a plate form, the container may have a flat form including a polygonal shape such as a quadrilateral or hexagonal shape, or a curve such as a round shape or an oval shape. More specifically, the container includes an inlet port-side container having an inlet port of a blood product and an outlet port-side container having an outlet port of a blood product and has a shape where both the containers sandwich the carrier directly or via a supporting body to divide the inside of the carrier into two parts, thus forming a flat filter. Alternatively, in the case of using a carrier in the cylindrical shape, the container is preferably in the cylindrical shape. More specifically, the container includes a cylindrical body where the carrier is packed, an inlet port-side header having an inlet port of a blood product, and an outlet port-side header having an outlet port of a blood product. The container has a shape, the inside of which is divided into two parts by potting processing such that a liquid introduced from the inlet port flows from the outer periphery in to the inner periphery (or from the inner periphery out to the outer periphery) of the cylindrical carrier, thus forming a cylindrical filter.

The term "blood product" in the present invention generically means a liquid including whole blood which may contain an abnormal prion protein or one or more blood components prepared from the whole blood, or a liquid obtained by adding an anticoagulant or preservative solution to the liquid. Specific examples thereof include, but are not limited to, a whole blood product, erythrocyte product, platelet product, plasma product, washed erythrocyte suspension, thawed concentrated erythrocyte solution, synthetic blood, platelet-rich plasmas, and buffy coat.

The term "whole blood product" in the present invention means a blood product obtained by adding a preservative solution or anticoagulant such as Citrate Phosphate Dextrose (CPD), Citrate Phosphate Dextrose Adenine-1 (CPDA-1), Citrate Phosphate-2-Dextrose (CP2D), Acid Citrate Dextrose Formula-A (ACD-A), Acid Citrate Dextrose Formula-B (ACD-B), or heparin to whole blood collected from a donor.

Hereinafter, a method of removing an abnormal prion protein from a blood product of the present invention is described, focusing on the procedures. First, an embodiment of a method of preparing various blood products is described, which is not intended to be limiting of the present invention.

(Preparation of Abnormal Prion Protein-Removed Whole Blood Product)

A preservative solution or anticoagulant such as CPD, CPDA-1, CP2D, ACD-A, ACD-B, or heparin is added to a collected whole blood, and the solution is filtered using a filter of the present invention to remove an abnormal prion protein from the whole blood, to thereby prepare an abnormal prion protein-removed whole blood product. The whole blood product is filtered using a system including at least a bag containing a blood product, a filter, and a bag for recovering an abnormal prion protein-removed blood product, which are aseptically connected via lines in this order (FIG. 1). The system may be connected to a blood collecting needle, a blood collecting bag, a bag for separating components after centrifugation, or a line for recovering a blood product remaining in the filter. An abnormal prion protein may be removed by filtration performed by passing a blood product to a filter via a tube from a bag containing the blood product placed at a position higher than the filter by force of gravitation, or by passing a blood product using an apparatus such as a pump from the inlet-port side of the filter under increased pressure and/or from the outlet side of the filter under reduced pressure. The filtration method may be applied to not only whole blood products but also other blood products.

In the case where an abnormal prion protein is removed before storage to prepare an abnormal prion protein-removed whole blood product, an abnormal prion protein is removed using the filter of the present invention at room temperature or in refrigeration preferably within 72 hours, more preferably within 24 hours, particularly preferably within 12 hours, most preferably within 8 hours after collecting of whole blood which is then stored at room temperature or in refrigeration. In the case where an abnormal prion protein is removed after storage to prepare an abnormal prion protein-removed whole blood product, an abnormal prion protein is removed using the filter within preferably 24 hours before use. In the present invention, a whole blood product containing neither abnormal prion protein nor leukocytes can be prepared.

(Preparation of Abnormal Prion Protein-Removed Erythrocyte Product)

A preservative solution or anticoagulant such as CPD, CPDA-1, CP2D, ACD-A, ACD-B, or heparin is added to a collected whole blood. Examples of the sequential separation method into components include: a method including removing an abnormal prion protein from whole blood and then performing centrifugation; and a method including centrifuging whole blood and then removing an abnormal prion protein from erythrocyte or erythrocyte and buffy coat (hereinafter, referred to a "BC").

In the case where centrifugation is performed after removal of an abnormal prion protein from whole blood, an abnormal prion protein-removed erythrocyte product is obtained by preparing an abnormal prion protein-removed whole blood, in the same way as in the preparation of the abnormal prion protein-removed whole blood product, centrifuging the abnormal prion protein-removed whole blood and recovering a concentrated erythrocyte in the lower layer.

In the case where whole blood is centrifuged before removal of an abnormal prion protein, there may be employed two centrifugation conditions: mild centrifugation conditions for separating the blood into erythrocytes and platelet-rich plasma (PRP) and strong centrifugation conditions for separating the blood into erythrocytes, BC, and platelet poor plasma (PPP). If necessary, a preservative solution such as Saline Adenine Glucose Mannitol solution (SAGM), Additive solution-1 (AS-1), Additive solution-3 (AS-3), Additive solution-5 (AS-5), or Mannitol Adenine Phosphate (MAP) is added to erythrocytes separated and recovered from the whole blood, or erythrocytes containing BC, and an erythrocyte product may be filtered using the filter of the present invention, to thereby prepare an abnormal prion protein-removed erythrocyte product.

In preparation of an abnormal prion protein-removed erythrocyte product, centrifugation is performed within preferably 72 hours, more preferably 48 hours, particularly preferably 24 hours, most preferably 12 hours of collecting of whole blood at room temperature or in refrigeration. In the case where an abnormal prion protein is removed before storage, an abnormal prion protein-removed whole blood product is prepared by removing an abnormal prion protein using a filter within preferably 120 hours, more preferably 72 hours, particularly preferably 24 hours, most preferably 12 hours of collection of blood from an erythrocyte product stored at room temperature or in refrigeration. In the case where an abnormal prion protein is removed after storage, the abnormal prion protein is removed from an erythrocyte product stored at room temperature or in refrigeration within preferably 24 hours before use, to thereby prepare an abnormal prion protein-removed erythrocyte product.

(Preparation of Abnormal Prion Protein-Removed Platelet Product)

A preservative solution or anticoagulant such as CPD, CPDA-1, CP2D, ACD-A, ACD-B, or heparin is added to a collected whole blood.

Examples of the sequential separation method into components include: a method including removing an abnormal prion protein from whole blood and then performing centrifugation; and a method including centrifuging whole blood and then removing an abnormal prion protein from PRP or platelet.

In the case where centrifugation is performed after removal of an abnormal prion protein from whole blood, an abnormal prion protein-removed platelet product is obtained by preparing an abnormal prion protein-removed whole blood, in the same way as in the preparation of the abnormal prion protein-removed whole blood product, centrifuging the abnormal prion protein-removed whole blood, recovering PRP in the upper layer, centrifuging the upper layer, and recovering a concentrated platelet (PC) in the lower layer.

In the case where whole blood is centrifuged before removal of an abnormal prion protein, there may be employed two centrifugation conditions: mild centrifugation conditions for separating the blood into erythrocytes and PRP and strong centrifugation conditions for separating the blood into erythrocytes, BC, and PPP. In the case of the mild centrifugation conditions, an abnormal prion protein-removed platelet product is prepared by filtering PRP separated from whole blood using a filter to remove an abnormal prion protein, centrifuging the filtrate again, and recovering PC in the lower layer, or by centrifuging PRP to separate platelet and PPP and filtering PC in the lower layer using a filter to remove an abnormal prion protein. In the case of the strong centrifugation, an abnormal prion protein-removed platelet product is prepared by, if necessary, adding a preservative solution or plasma to BC which has been separated from whole blood and collected in an amount of one to several tens of units, centrifuging the solution, recovering the upper layer to prepare a concentrated platelet, and filtering the platelet using a filter to remove an abnormal prion protein.

In preparation of an abnormal prion protein-removed platelet product, whole blood stored at room temperature is collected within preferably 24 hours, more preferably 12 hours, particularly preferably 8 hours of collecting of whole blood. In the case where an abnormal prion protein is removed, an abnormal prion protein-removed platelet whole blood product is prepared by removing an abnormal prion protein using a filter within preferably 120 hours, more preferably 78 hours, particularly preferably 24 hours, most preferably 12 hours of collection of a platelet product which is then stored at room temperature. In the case where an abnormal prion protein is removed after storage, the abnormal prion protein is removed by a filter from a platelet product being stored at room temperature or in refrigeration within preferably 24 hours before use, to thereby prepare an abnormal prion protein-removed platelet product.

(Preparation of Abnormal Prion Protein-Removed Plasma Product)

A preservative solution or anticoagulant such as CPD, CPDA-1, CP2D, ACD-A, ACD-B, or heparin is added to a collected whole blood.

Examples of the subsequent separation method into components include: a method including removing an abnormal prion protein from whole blood and then performing centrifugation; and a method including centrifuging whole blood and then removing an abnormal prion protein from PPP or PRP.

In the case where centrifugation is performed after removal of an abnormal prion protein from whole blood, a leukocyte-removed plasma product is obtained by preparing an abnormal prion protein-removed whole blood, in the same way as in the preparation of the abnormal prion protein-removed whole blood product, centrifuging the abnormal prion protein-removed whole blood, and recovering plasma in the upper layer.

In the case where whole blood is centrifuged before removal of an abnormal prion protein, there may be employed two centrifugation conditions: mild centrifugation conditions for separating the blood into erythrocytes and PRP and strong centrifugation conditions for separating the blood into erythrocytes, BC, and PPP. In the case of the mild centrifugation conditions, an abnormal prion protein-removed plasma product is prepared by filtering PRP using a filter to remove an abnormal prion protein, after filtering of PRP, centrifuging the filtrate again, and recovering PPP in the supernatant, or by separating PRP into PPP and platelet by centrifugation and filtering PPP using a filter to remove an abnormal prion protein. In the case of the strong centrifugation conditions, an abnormal prion protein-removed plasma product is prepared by filtering PPP using a filter to remove an abnormal prion protein.

In preparation of an abnormal prion protein-removed plasma product, whole blood stored at room temperature or in refrigeration is centrifuged within preferably 72 hours, more preferably 48 hours, particularly preferably 24 hours, most preferably 12 hours of collecting of whole blood. Alternatively, an abnormal prion protein-removed plasma product is prepared by removing an abnormal prion protein using a filter within preferably 120 hours, more preferably 72 hours, particularly preferably 24 hours, most preferably 12 hours of collection of blood from a plasma product which is then stored at room temperature or in refrigeration. In the case where an abnormal prion protein is removed after storage, the abnormal prion protein is removed by a filter from a plasma product stored at room temperature or in refrigeration within preferably 24 hours before use, to thereby prepare an abnormal prion protein-removed plasma product.

The term "leukocyte removal filter" in the present invention means a filter capable of removing leukocytes by filtration of a blood product at a rate of 99% or more, preferably 99.9% or more, more preferably 99.99% or more. In the case where the capability of the filter is rephrased as the leukocyte-removing capability, the filter shows a value calculated according to the following formula (1). That is, the filter has leukocyte-removing capability of 2 or more, preferably 3 or more, more preferably 4 or more.

$$\text{Leukocyte-removing capability} = -\log_{10}\{[\text{Concentration of leukocyte(cells/μL)(blood after filtration)}]/[\text{Concentration of leukocyte(cells/μL)(blood before filtration)}]\} \quad (1)$$

The method of sterilizing the filter of the present invention includes: ethylene oxide gas sterilization; radiation sterilization such as γ-ray sterilization or electron beam sterilization; and autoclave sterilization. The radiation sterilization or autoclave sterilization is more preferable. To provide high abnormal prion protein-removing capability from a whole blood product, a filter is preferably subjected to both radiation sterilization and autoclave sterilization. There is no order between the radiation sterilization and autoclave sterilization, but more preferably, the autoclave sterilization is performed after the radiation sterilization. Use of a polymer-coated carrier subjected to the autoclave sterilization may decrease the amount of an abnormal prion protein adsorbed on the carrier coated with the polymer in a whole blood product. This is probably caused by competitive adsorption with proteins in the whole blood product because the autoclave sterilization induces no changes in chemical properties of the polymer on the surface of the carrier. On the other hand, in the case of the radiation sterilization, high prion-removing capability can be provided even in a whole blood product. The reason is not clear, but it is conceivable that the radiation sterilization for the filter causes changes in the chemical properties of the polymer on the surface of the carrier, resulting in preferable charge state and composition balance of the three units in the polymer for adsorption of the abnormal prion protein. However, surprisingly, the inventors of the present invention have found out that high abnormal prion protein-removing capability can be provided in a whole blood product even if the autoclave sterilization is performed if that is after the radiation sterilization. It is estimated that, if the autoclave sterilization is performed after the radiation sterilization, adsorption specificity for an abnormal prion protein is maintained to provide high abnormal prion protein-removing capability, regardless of the autoclave sterilization. In the case of using an inline-type set, if only a filter is subjected to the radiation sterilization in advance, high abnormal prion protein-removing capability can be provided even after the autoclave sterilization.

EXAMPLES

The present invention is described in more detail by examples, which are not intended to be limiting of the present invention.

The numerical values used in examples and comparative examples were measured by the following methods.

(Specific Surface Area of Filter Material)

The term "specific surface area (m$^2$/g)" in the present invention means a surface area per unit weight of a nonwoven fabric, which is determined by a gas adsorption method (BET method) using "Accusorb 2100" (manufactured by Shimadzu Corp.) or an equivalent. The specific surface area is determined by: filling a sample tube with 0.50 g to 0.55 g of a carrier; deaerating the tube at a reduced pressure level of $1 \times 10^{-4}$ mmHg (at room temperature) for 20 hours in the apparatus Accusorb; adsorbing krypton gas having a known adsorption area as an adsorption gas to the surface of a nonwoven fabric at a temperature equivalent to the liquid nitrogen temperature; calculating the total surface area in the nonwoven fabric based on the adsorbed amount; and dividing the total surface area by the weight of the nonwoven fabric.

(Measurement of Average Fiber Diameter)

Electron microscopic photographs were taken at five points randomly of a nonwoven fabric. A transparent sheet on which grid is drawn was layered on each photograph. The diameter of the thread at the crossing points of the grid was measured (n=100), and the average diameter was determined by converting the measured diameter using, as a scale, polystyrene latex of which the diameter is known.

(Polymer Amount Per Unit Area of the Total Surface Area of Material)

The term "total surface area ($m^2$) of the material" in the present invention refers to a value obtained by multiplying the weight (g) of the material by the specific surface area ($m^2$/g) of the material. The polymer amount (mg/$m^2$) per unit area ($m^2$) of the total surface area of the material of the present invention is determined by NMR analysis of a solution of a certain area (weight) of the material dissolved in a deuterated solvent common to the carrier and coating agent. For example, a prescribed amount of a material including a polyester nonwoven fabric coated with a polymer containing methyl methacrylate, dimethylaminoethyl methacrylate, and 2-hydroxy methacrylate was dissolved in deuterated 1,1,1,3,3,3-hexafluoro-2-propanol. The ratio of intensity of the signals clearly belonging to the nonwoven fabric (e.g. proton on benzene ring) and the signals clearly belonging to the coating material (e.g. proton on the methyl group adjacent to methyl methacrylate) was determined. Then, the polymer amount per unit weight of the nonwoven fabric was determined from the ratio of intensity and a separately determined copolymerization composition of the coating material. The polymer amount per unit weight of the nonwoven fabric can be converted into the polymer amount per total surface area of the material using a specific surface area of the material filled in the filter.

(Blood Filtration Test: Examples 1 to 13 and Comparative Examples 1 to 9)

Erythrocyte products were used as blood products for blood evaluation, and each product was obtained by: adding 14 mL of a CPD solution serving as an anticoagulant to 100 mL of blood immediately after collecting the blood; blending the mixture; storing the mixture in refrigeration for 72 hours; centrifuging the mixture; adding SAGM to the separated erythrocytes containing BC; and allowing the mixture to stand for 1 hour (hereinafter, referred to as "blood before filtration").

The filter used for evaluation was obtained by filling a container with a polyester nonwoven fabric C (average fiber diameter: 1.2 μm, weight of the substrate per unit area: 40 g/$m^2$, specific surface area: 1.47 $m^2$/g) coated with a polymer prepared in each of examples and comparative examples (without coating in Comparative Example 6). A column (effective filtration area: 1.3 $cm^2$) was filled with eight coated nonwoven fabrics, and a syringe filled with blood before filtration was connected to the inlet of the column via a vinyl chloride tube (inner diameter: 3 mm, outer diameter: 4.2 mm). Then, the blood was passed through the column at a flow rate of 0.175 mL/min using a syringe pump in a refrigerator and recovered in an amount of 3 mL (hereinafter, referred to as "blood after filtration"). The coated nonwoven fabrics (without coating in Comparative Example 6) were subjected to: γ-ray sterilization at 25 KGy in Examples 1 to 5 and 11 and Comparative Examples 1 to 9; electron beam sterilization at 30 KGy in Examples 8 and 12; autoclave sterilization at 115° C. for 59 minutes in Examples 6, 7, 10, and 13; electron beam sterilization at 30 KGy and then autoclave sterilization at 115° C. for 59 minutes in Example 9; and no sterilization in Comparative Example 10.

[Leukocyte-Removing Capability]

The leukocyte-removing capability was calculated by Formula (1) above based on leukocyte concentrations before and after filtration. The leukocyte concentrations were measured by a flow cytometry method (apparatus: FACSCalibur manufactured by BECTON DICKINSON) for 100 μL of each blood sample using a Leucocount kit containing beads (manufactured by Nippon Becton Dickinson Company, Ltd.).

[Blood Processing Pressure]

The blood processing pressure was measured at the end of filtration using a pressure indicator connected to the tube on the inlet side of the column.

[Hemolysis Level of Blood after Filtration]

The Hemolysis Level of blood after filtration was calculated based on a free hemoglobin level in plasma with respect to the total hemoglobin level in an erythrocyte product after a lapse of 42 days from filtration.

The specific method of calculating the Hemolysis Level is as follows.

(1) The total hemoglobin content (g/dL) and hematocrit level (%) in an erythrocyte product after filtration are determined using an automatic blood cell counter.

(2) A sample of an erythrocyte product after filtration is recovered in an amount of 2 mL and centrifuged at 1,750×g for 10 minutes.

(3) Absorbances of the supernatant are measured by scanning at wavelengths between 630 nm and 500 nm using a spectrophotometer.

(4) The free hemoglobin concentration in the plasma is calculated according to a method described in Clin. Biochem. 8, 96-102 (1975).

(5) The Hemolysis Level is calculated by Formula (2) below.

$$\text{Hemolysis Level}(\%) = (100 - \text{Hematocrit level}(\%)) \times (\text{Free hemoglobin concentration}(g/dL))/\text{Total hemoglobin concentration}(g/dL) \quad (2)$$

(Evaluation of Abnormal Prion Protein-Removing Capability: Examples 1 to 13 and Comparative Examples 1, 3, 5 to 8, and 10)

[Preparation of Filter]

A polyester nonwoven fabric P (average fiber diameter: 12 μm, weight of the substrate per unit area: 30 g/$m^2$, specific surface area: 0.24 $m^2$/g), a polyester nonwoven fabric A (average fiber diameter: 2.5 μm, weight of the substrate per unit area: 60 g/$m^2$, specific surface area: 0.8 $m^2$/g), a polyester nonwoven fabric B (average fiber diameter: 1.8 μm, weight of the substrate per unit area: 60 g/$m^2$, specific surface area: 1.1 $m^2$/g), and a polyester nonwoven fabric C (average fiber diameter: 1.2 μm, weight of the substrate per unit area: 40 g/$m^2$, specific surface area: 1.47 $m^2$/g) coated with a polymer prepared in each of examples and comparative examples (without coating in Comparative Example 6) were used as filter media. The filter media P, A, B, and C were laminated in P-A-B-C order from the upstream side, and B' (the same filter medium as B), A' (the same filter medium as A), and P' (the same filter medium as P) were further laminated on the downstream side, to thereby prepare a filter medium having a symmetric structure of P-A-B-C-B'-A'-P'. The resultant filter medium was sandwiched between flexible vinyl chloride resin sheets with ports serving as an inlet or outlet of blood, and the peripheral border between the filter medium and the flexible sheet was adhered and integrated using a high frequency welding device, to thereby prepare a filter with an effective filtration area of 56 $cm^2$.

The resultant filters were subjected to: γ-ray sterilization at 25 KGy in Examples 1 to 5 and 11 and Comparative Examples 1 to 9; electron beam sterilization at 30 KGy in Examples 8 and 12; autoclave sterilization at 115° C. for 59 minutes in Examples 6, 7, 10, and 13; electron beam sterilization at 30 KGy and then autoclave sterilization at 115° C. for 59 minutes in Example 9; and no sterilization in Comparative Example 10.

[Preparation of Scrapie-Infected Hamster Brain]
An abnormal prion protein named Sc237, derived from a passage of the 263K hamster to be used for developing scrapie was inoculated into a hamster, and after a lapse of 65 days to 70 days, the brain of the hamster was removed and used as a scrapie-infected hamster brain.

[Preparation of Homogenate]
The scrapie-infected hamster brain was sonicated in 320 mM sucrose to prepare a 10 weight (g)/volume (100 ml) % (hereinafter, referred to as "W/V %") homogenate. The homogenate was centrifuged at 4° C. and 80×g for 1 minute and used as a homogenate to be added (hereinafter, abbreviated as "homogenate").

[Preparation of Microsomal Fraction]
The homogenate was centrifuged at 5,000×g for 20 minutes, and the supernatant was further centrifuged at 100,000×g for 1 hour. The resultant precipitates were resuspended in a solution (150 mM NaCl, 20 mM Tris-HCl, pH 7.4), and the suspension was centrifuged at 100,000×g for 1 hour. The resultant precipitates were resuspended in pH 7.4 PBS (Phosphate-Buffered Saline) to prepare a microsomal fraction to be added (hereinafter, abbreviated as "microsomal fraction").

[Protease K Concentration Determination Method 1: Examples 1, 2, 4, and 13]
(Sample not Treated with Protease K)
50 μL of the homogenate and 50 μL of an erythrocyte product containing the homogenate were separately mixed in 450 μL each of a sample buffer, and the resultant mixtures were incubated at 100° C.±5° C. for 5 to 10 minutes or at 70° C. to 80° C. for 10 to 15 minutes.
(Sample Treated with Protease K)
50 μL of the homogenate and 50 μL of an erythrocyte product containing the homogenate were separately mixed in solutions with different concentrations of protease K and 0.6 to 1% Sarkosyl, and the mixtures were incubated at 37° C.±4° C. for 1 hour±5 minutes. 300 μL of the sample buffer was added thereto, and the mixtures were separately incubated at 100° C.±5° C. for 5 to 10 minutes or at 70° C. to 80° C. for 10 to 15 minutes.
The samples without protease K treatment and samples with protease K treatment were analyzed by Western blotting to determine minimum concentrations of protease K so that proteins capable of nonspecifically reacting with an antibody and normal prion protein were completely decomposed by protease K and hence not detected, nevertheless an abnormal prion protein was detected.

[Protease K Concentration Determination Method 2: Examples 3 and 6 and Comparative Examples 5, 6, and 10]
(Sample not Treated with Protease K)
5 mL of a blood product containing the microsomal fraction and 5 mL of a blood product containing a normal prion protein were separately centrifuged at 4,000×g for 20 minutes. Then, 3 mL of the supernatants were centrifuged at 100,000×g and 4° C.±2° C. for 1 hour. The resultant precipitates were resuspended in 100 μL of a sample buffer, and the suspensions were incubated at 100° C.±5° C. for 5 to 10 minutes.
(Sample Treated with Protease K)
5 mL of a blood product containing the microsomal fraction and 5 mL of a blood product containing a normal prion were separately centrifuged at 4,000×g for 20 minutes. Solutions with different concentrations of protease K were mixed in 3 mL of the supernatants, and the mixtures were centrifuged at 100,000×g and 4° C.±2° C. for 1 hour. The resultant precipitates were resuspended in 100 μL of the sample buffer, and the suspensions were incubated at 100° C.±5° C. for 5 to 10 minutes.
The samples without protease K treatment and samples with protease K treatment were analyzed by Western blotting to determine minimum concentrations of protease K so that proteins capable of nonspecifically reacting with an antibody and normal prion were completely decomposed by protease K and hence not detected, nevertheless an abnormal prion protein was detected.

[Protease K Concentration Determination Method 3: Example 5 and Comparative Examples 1, 3, 7, and 8]
(Sample not Treated with Protease K)
50 μL of plasma containing a microsomal fraction and 50 μL of plasma were separately mixed in 50 μL of a sample buffer, and the mixtures were incubated at 100° C.±5° C. for 5 to 10 minutes.
(Sample Treated with Protease K)
Solutions with different concentrations of protease K were mixed in 3 mL of plasma containing a homogenate prepared from the brain of a scrapie-uninfected hamster and 3 mL of plasma containing a microsomal fraction prepared from the brain of a scrapie-infected hamster, and the mixtures were centrifuged at 20,000×g and 4° C.±2° C. for 1 hour. After centrifugation, 100 μL of a sample buffer was added to the resultant precipitates and was allowed to react at 100° C.±5° C. for 5 to 10 minutes. The samples without protease K treatment and samples with protease K treatment were analyzed by Western blotting to determine minimum concentrations of protease K so that proteins capable of nonspecifically reacting with an antibody and normal prion were completely decomposed by protease K and hence not detected, nevertheless an abnormal prion protein was detected.

[Protease K Concentration Determination Method 4: Examples 7 to 9]
A whole blood product after removal of leukocytes was centrifuged at 4,000×g for 30 minutes, and 1.3 ml of a microsomal fraction was added to 11.7 ml of the resultant supernatant (hereinafter, referred to as "Supplemented Prefiltration Blood"), while no compound was added to 12 ml of the supernatant (hereinafter, referred to as "Unsupplemented Prefiltration Blood")
(Sample not Treated with Protease K)
3 mL of Supplemented Prefiltration Blood and 3 mL of Unsupplemented Prefiltration Blood were separately centrifuged at 100,000×g and 4° C.±2° C. for 1 hour. The resultant precipitates were resuspended in 100 μL of a sample buffer, and the suspensions were incubated at 100° C.±5° C. for 5 to 10 minutes.
(Sample Treated with Protease K)
1 to 2% (w/v) Sarkosyl and solutions with different concentrations of protease K were mixed in 3 mL of the Supplemented Prefiltration Blood or 3 mL of the Unsupplemented Prefiltration Blood, and the mixtures were centrifuged at 100,000×g and 4° C.±2° C. for 1 hour. The resultant precipitates were resuspended in 100 μL of the sample buffer, and the suspensions were separately incubated at 100° C.±5° C. for 5 to 10 minutes. The samples without protease K treatment and samples with protease K treatment were analyzed by Western blotting to determine minimum concentrations of protease K so that proteins capable of nonspecifically reacting with an antibody and normal prion protein were completely undetectable due to protease K, nevertheless an abnormal prion protein was detected.

[Protease K Concentration Determination Method 5: Examples 10 to 12]
An erythrocyte product after removal of leukocytes was centrifuged at 4,000×g for 30 minutes, and 1.3 ml of a microsomal fraction was added to 11.7 ml of the resultant supernatant (hereinafter, referred to as "Supplemented Prefiltration Blood"), while no compound was added to 12 ml of the supernatant (hereinafter, referred to as "Unsupplemented Prefiltration Blood")
(Sample not Treated with Protease K)
3 mL of Supplemented Prefiltration Blood and 3 mL of Unsupplemented Prefiltration Blood were separately centrifuged at 100,000×g and 4° C.±2° C. for 1 hour. The resultant precipitates were resuspended in 100 μL of a sample buffer, and the suspensions were incubated at 100° C.±5° C. for 5 to 10 minutes.
(Sample Treated with Protease K)
1 to 2% (w/v) Sarkosyl and solutions with different concentrations of protease K were mixed in 3 mL of the Supplemented Prefiltration Blood or 3 mL of the Unsupplemented Prefiltration Blood, and the mixtures were centrifuged at 100,000×g and 4° C.±2° C. for 1 hour. The resultant precipitates were resuspended in 100 μL of the sample buffer, and the suspensions were separately incubated at 100° C.±5° C. for 5 to 10 minutes. The samples without protease K treatment and samples with protease K treatment were analyzed by Western blotting to determine minimum concentrations of protease K so that proteins capable of nonspecifically reacting with an antibody and a normal prion protein were completely undetectable due to protease K, nevertheless an abnormal prion protein was detected.

[Abnormal Prion Protein-Removing Capability Test 1: Examples 1, 2, 4, and 13]

An erythrocyte product manufactured under a European standard was purchased and used. A homogenate was added to the erythrocyte product in an amount of 13 mL with respect to 1 unit of the erythrocyte product at room temperature, to thereby prepare Supplemented Prefiltration Blood. The resultant solution was filtered using a filter including the polyester nonwoven fabric C coated with the polymers, prepared in each of Examples 1, 2, 4, and 13 by gravity from a height of 100 cm, and blood was recovered to prepare an Supplemented Postfiltration Blood. First, each of the Supplemented Prefiltration Blood and the Supplemented Postfiltration Blood was dissolved in a cell lysate (prepared by dissolving 11.45 g of ammonium oxalate, 433 mg of potassium dihydrogen phosphate, and 567 mg of disodium monohydrogen phosphate in 1 L of distilled water for injection). Each of the Supplemented Prefiltration Blood and the Supplemented Postfiltration Blood was mixed with the cell lysate at a volume ratio of 1:3, and the mixture was dissolved at room temperature for 30 minutes. After dissolution, sonication (15±5 seconds each time, 50±10% power) was performed three times with pauses of 30±10 seconds. A protease K solution with a concentration determined in the Protease K concentration determination method 1 and 0.6 to 1% Sarkosyl were added to each of the Supplemented Prefiltration Blood and the Supplemented Postfiltration Blood, and decomposition with protease K was performed at 37° C.±3° C. for 1 hour±5 minutes and then stopped by adding 10 mM Pefabloc. Thereafter, the resultant mixture was centrifuged at 100,000×g and 4° C.±2° C. for 1 hour, and 500 μl of a sample buffer was added to the resultant precipitates, followed by incubation at 100° C.±5° C. for 5 to 10 minutes or at 70 to 80° C. for 10 to 15 minutes.

[Abnormal Prion Protein-Removing Capability Test 2: Example 3 and Comparative Examples 5 and 6]

A leukocyte-removed erythrocyte product manufactured under a European standard was purchased and used. The product was stored for one or two days in a 4° C. refrigerator, and 12 mL of a microsomal fraction was added to 1 unit of the leukocyte-removed erythrocyte product at room temperature, to thereby prepare a Supplemented Prefiltration Blood. The resultant solution was filtered using a filter including the polyester nonwoven fabric C coated with the polymer prepared in each of Example 3 and Comparative Examples 5 and 6 (coated with no polymer in Comparative Example 6) by gravity from a height of 100 cm, and blood was recovered to prepare an Supplemented Postfiltration Blood. The Supplemented Prefiltration Blood and Supplemented Postfiltration Blood were centrifuged at 4,000×g for 30 minutes, and the supernatants were divided into aliquots. Protease K was added to the supernatants at a concentration of 1,000 μg/mL, and the mixtures were centrifuged at 100,000×g and 4° C.±2° C. for 1 hour. After centrifugation, the precipitates were resuspended in 100 μL of a sample buffer, and the suspensions were incubated at 100° C.±5° C. for 5 to 10 minutes.

[Abnormal Prion Protein-Removing Capability Test 3: Example 5 and Comparative Examples 1, 3, 7, and 8]

Fresh frozen plasma manufactured under a European standard was purchased and dissolved on the day of filtration at 37° C., and a microsomal fraction was added in a volume of 8.6% with respect to the weight of the plasma, to thereby prepare an Supplemented Prefiltration Blood. The Supplemented Prefiltration Blood (150 g±2 g) was filtered using a filter including the polyester nonwoven fabric coated with the polymer prepared in each of Example 5 and Comparative Examples 1, 3, 7, and 8 by gravity from a height of 100 cm, and the blood was recovered to prepare an Supplemented Postfiltration Blood. To 100 μL of each of the Supplemented Prefiltration Blood and the Supplemented Postfiltration Blood was added protease K at a concentration of 600 μg/mL, and the mixtures were centrifuged at 20,000×g and 4° C.±2° C. for 1 hour. The precipitates were resuspended in 100 μL of a sample buffer, and the suspensions were incubated at 100° C.±5° C. for 5 to 10 minutes.

[Abnormal Prion Protein-Removing Capability Test 4: Example 6 and Comparative Example 10]

A leukocyte-removed whole blood product manufactured under a European standard was purchased and used. The thus obtained whole blood product after leukocyte removal was stored for one day in a 4° C. refrigerator, and 28 mL of a microsomal fraction was added to 1 unit of the leukocyte-removed whole blood product at room temperature, to thereby prepare an Supplemented Prefiltration Blood. The resultant solution was filtered using a filter including the polyester nonwoven fabric coated with the polymer prepared in Example 6 and the filter of Comparative Example 10 by gravity from a height of 100 cm, and blood was recovered to prepare an Supplemented Postfiltration Blood. The Supplemented Prefiltration Blood and Supplemented Postfiltration Blood were centrifuged at 4,000×g for 30 minutes, and the supernatants were divided into aliquots. Protease K was added to the supernatants at a concentration of 1,000 μg/mL, and the mixtures were centrifuged at 100,000×g and 4° C.±2° C. for 1 hour. After centrifugation, the precipitates were resuspended in 100 μL of a sample buffer, and the suspensions were incubated at 100° C.±5° C. for 5 to 10 minutes.

[Abnormal Prion Protein-Removing Capability Test 5: Example 7, 8, and 9]

A leukocyte-removed whole blood cell product manufactured under European standards was purchased and used. The product was stored for 1 to 3 days in a refrigerator at 4° C., and three units of the leukocyte-removed erythrocyte product were placed in one blood bag. Then, 84 mL of a microsomal fraction was added thereto at room temperature to prepare an Supplemented Prefiltration Blood. The Supplemented Prefiltration Blood was divided into three parts, and the resultant Supplemented Prefiltration Blood was filtered using a filter including the polyester nonwoven fabric C coated with the polymer prepared in each of Examples 7, 8, and 9 by gravity from a height of 100 cm, and the blood was recovered, to thereby prepare an Supplemented Postfiltration Blood. The Supplemented Prefiltration Blood and Supplemented Postfiltration Blood were centrifuged at 4,000×g for 30 minutes, and the supernatants were divided into aliquots. Protease K was added to the supernatants so as to be a concentration of 25 U/mL, and the mixtures were centrifuged at 100,000×g and 4° C.±2° C. for 1 hour. After centrifugation, the precipitates were resuspended in 100 μL of a sample buffer, and the suspensions were incubated at 100° C.±5° C. for 5 to 10 minutes.

[Abnormal Prion Protein-Removing Capability Test 6: Examples 10, 11 and 12]

A leukocyte-removed erythrocyte product manufactured under European standards was purchased and used. The product was stored for two to four days in a refrigerator at 4° C., and 9.5 mL of a microsomal fraction was added to 1 unit of the leukocyte-removed erythrocyte product at room temperature, to thereby prepare an Supplemented Prefiltration Blood. The resultant solution was filtered using a filter including the polyester nonwoven fabric C coated with the polymer prepared in each of Examples 10, 11, and 12 by gravity from a height of 100 cm, and blood was recovered to prepare an Supplemented Postfiltration Blood. The Supplemented Prefiltration Blood and Supplemented Postfiltration Blood were centrifuged at 4,000×g for 30 minutes, and the supernatants were divided into aliquots. Protease K was added to the supernatants so as to be a concentration of 25 U/mL, and the mixtures were centrifuged at 100,000×g and 4° C.±2° C. for 1 hour. After centrifugation, the precipitates were resuspended in 100 μL of a sample buffer, and the suspensions were incubated at 100° C.±5° C. for 5 to 10 minutes.

[Analysis of Abnormal Prion Protein Titer]

The blood products of the Supplemented Prefiltration Blood and the Supplemented Postfiltration Blood were added in the sample buffer, and the mixtures were heated, followed by detection of an abnormal prion protein by a general Western blot method using 3F4 capable of specifically binding to a prion protein as a primary antibody. Detection for all the Supplemented Prefiltration Blood and the Supplemented Postfiltration Blood was repeated several times in a continuous three-fold dilution series, and $ED_{50}$ was determined by the method of Spearman (Brit. J. of Psychology 1908; 2: 227 ff.) and Kaerber (Naunyn Schmiedeberg's Arhc. Exp. Path. Pharmak. 1931; 152: 380 ff.). Then, each value was converted into $ED_{50}$ per unit volume (1 mL), and the logarithm of the value was calculated as a titer. The method of calculating $ED_{50}$ is as follows.

$$ED_{50}=10^{-Y_0-d/2+d\cdot\Sigma EY_i}$$ [Formula 1]

Y0: positive exponent of the highest sample dilution with positive test results in all parallel dilutions
D: Logarithm of dilution step
ΣYi: sum of percentage of sample where abnormal prion was detected when the sample was diluted Y0:-fold or more

[Abnormal Prion Protein-Removing Capability]

The abnormal prion protein-removing capability is determined by the following Formula (4).

Abnormal prion protein-removing capability=Titer of abnormal prion protein(Supplemented Prefiltration Blood)−Titer of abnormal prion protein (Supplemented Postfiltration Blood)  (4)

Example 1

Polymerization was performed by adding dropwise an ethanol solution obtained by dissolving the polymerizable monomers and a diazo-type initiator to ethanol used as a polymerization solvent while stirring at 78° C. in a nitrogen atmosphere. The charged polymerizable monomers include 20 mol % of methyl methacrylate (hereinafter, abbreviated as "MMA") used as a hydrophobic polymerizable monomer, 5 mol % of dimethylaminoethyl methacrylate (hereinafter, abbreviated as "DM") used as a polymerizable monomer containing a basic nitrogen-containing part, 75 mol % of 2-hydroxyethyl methacrylate (hereinafter, abbreviated as "HEMA") used as a monomer containing a protonic neutral hydrophilic part. The polymer solution was purified using an excessive amount of water and dried under reduced pressure. The copolymerization composition of the polymer was analyzed by 1H-NMR. The results were almost in accord with the charged polymerizable monomer composition, with the copolymerization compositions of MMA, DM, and HEMA in the polymer being 20 mol %, 5 mol %, and 75 mol %, respectively. The weight average molecular weight (Mw) was 210,000. Ethanol was used as a coating solvent, and the polymer concentration of 0.8 W/V % was employed. The polymer solution with the above concentration was coated to a polyester nonwoven fabric C used as a material. The coated amount was 21 mg/m² per unit area on the entire surface area of the material. In the same way as above, a leukocyte-removing capability test, a pressure test during recovery, a hemolysis test after filtration, and an abnormal prion protein-removing capability test 1 were performed. The leukocyte-removing capability, blood processing pressure, Hemolysis Level, and abnormal prion protein-removing capability were found to be 4.12, 9.8 kPa, 0.2%, and 2.0 or more, respectively.

Example 2

Polymerization, purification, and drying were carried out in the same manner as in Example 1, except for using a monomer charge ratio of MMA 20 mol %, DM 13 mol %, and HEMA 67 mol %. The copolymerization composition of the polymer was analyzed by 1H-NMR. The copolymerization compositions of MMA, DM, and HEMA in the polymer were 20 mol %, 13 mol %, and 67 mol %, respectively. The weight average molecular weight (Mw) was 250,000. The polymer solution with a polymer concentration of 0.8 W/V % in ethanol used as a coating solvent was coated to the polyester nonwoven fabric C. The coated amount was 22 mg/m² per unit area on the entire surface area of the material. In the same way as above, a leukocyte-removing capability test, a pressure test during recovery, a hemolysis test after filtration, and an abnormal prion protein-removing capability test 1 were performed. The leukocyte-removing capability, blood processing pressure, Hemolysis Level, and abnormal prion protein-removing capability were found to be 5.68, 8.1 kPa, 0.5%, and 2.0 or more, respectively.

Example 3

Polymerization, purification, and drying were carried out in the same manner as in Example 1, except for using a monomer charge ratio of MMA 30 mol %, DM 10 mol %, and HEMA 60 mol %. The copolymerization composition of the polymer was analyzed by 1H-NMR. The copolymerization compositions of MMA, DM, and HEMA in the polymer were 30 mol %, 10 mol %, and 60 mol %, respectively. The weight average molecular weight (Mw) was 210,000. The polymer solution with a polymer concentration of 0.8 W/V % in ethanol used as a coating solvent was coated to the polyester nonwoven fabric C. The coated amount was 20 mg/m² per unit area on the entire surface area of the material. In the same way as above, a leukocyte-removing capability test, a pressure test during recovery, a hemolysis test after filtration, and an abnormal prion protein-removing capability test 2 were performed. The leukocyte-removing capability, blood processing pressure, Hemolysis Level, and abnormal prion protein-removing capability were found to be 5.68, 11.4 kPa, 0.4%, and 3.8, respectively.

Example 4

Polymerization, purification, and drying were carried out in the same manner as in Example 1, except for using a monomer charge ratio of MMA 40 mol %, DM 5 mol %, and HEMA 55 mol %. The copolymerization composition of the polymer was analyzed by 1H-NMR. The copolymerization compositions of MMA, DM, and HEMA in the polymer were 40 mol %, 5 mol %, and 55 mol %, respectively. The weight average molecular weight (Mw) was 170,000. The polymer solution with a polymer concentration of 0.8 W/V % in ethanol used as a coating solvent was coated to the polyester nonwoven fabric C. The coated amount was 22 mg/m$^2$ per unit area on the entire surface area of the material. In the same way as above, a leukocyte-removing capability test, a pressure test during recovery, a hemolysis test after filtration, and an abnormal prion protein-removing capability test 1 were performed. The leukocyte-removing capability, blood processing pressure, Hemolysis Level, and abnormal prion protein-removing capability were found to be 5.17, 12.5 kPa, 0.3%, and 2.0 or more, respectively.

Example 5

Polymerization, purification, and drying were carried out in the same manner as in Example 1, except for using a monomer charge ratio of MMA 40 mol %, DM 13 mol %, and HEMA 47 mol %. The copolymerization composition of the polymer was analyzed by 1H-NMR. The copolymerization compositions of MMA, DM, and HEMA in the polymer were 40 mol %, 13 mol %, and 47 mol %, respectively. The weight average molecular weight (Mw) was 180,000. The polymer solution with a polymer concentration of 0.8 W/V % in ethanol used as a coating solvent was coated to the polyester nonwoven fabric C. The coated amount was 22 mg/m$^2$ per unit area on the entire surface area of the material. In the same way as above, a leukocyte-removing capability test, a pressure test during recovery, a hemolysis test after filtration, and an abnormal prion protein-removing capability test 3 were performed. The leukocyte-removing capability, blood processing pressure, Hemolysis Level, and abnormal prion protein-removing capability were found to be 5.68, 10.9 kPa, 0.5%, and 2.4, respectively.

Example 6

Polymerization, purification, and drying were carried out in the same manner as in Example 1, except for using a monomer charge ratio of MMA 30 mol %, DM 10 mol %, and HEMA 60 mol %. The copolymerization composition of the polymer was analyzed by 1H-NMR. The copolymerization compositions of MMA, DM, and HEMA in the polymer were 30 mol %, 10 mol %, and 60 mol %, respectively. The weight average molecular weight (Mw) was 210,000. The polymer solution with a polymer concentration of 0.8 W/V % in ethanol used as a coating solvent was coated to the polyester nonwoven fabric C. The coated amount was 20 mg/m$^2$ per unit area on the entire surface area of the material. In the same way as above, a leukocyte-removing capability test, a pressure test during recovery, a hemolysis test after filtration, and an abnormal prion protein-removing capability test 4 were performed. The leukocyte-removing capability, blood processing pressure, Hemolysis Level, and abnormal prion protein-removing capability were found to be 5.86, 13.2 kPa, 0.4%, and 1.5, respectively.

Example 7

Polymerization, purification, and drying were carried out in the same manner as in Example 1, except for using a monomer charge ratio of MMA 30 mol %, DM 10 mol %, and HEMA 60 mol %. The copolymerization composition of the polymer was analyzed by 1H-NMR. The copolymerization compositions of MMA, DM, and HEMA in the polymer were 30 mol %, 10 mol %, and 60 mol %, respectively. The weight average molecular weight (Mw) was 210,000. The polymer solution with a polymer concentration of 0.8 W/V % in ethanol used as a coating solvent was coated to the polyester nonwoven fabric C. The coated amount was 20 mg/m$^2$ per unit area on the entire surface area of the material. In the same way as above, a leukocyte-removing capability test, a pressure test during recovery, a hemolysis test after filtration, and an abnormal prion protein-removing capability test 5 were performed. The leukocyte-removing capability, blood processing pressure, Hemolysis Level, and abnormal prion protein-removing capability were found to be 5.12, 11.5 kPa, 0.3%, and 1.2, respectively.

Example 8

Polymerization, purification, and drying were carried out in the same manner as in Example 1, except for using a monomer charge ratio of MMA 30 mol %, DM 10 mol %, and HEMA 60 mol %. The copolymerization composition of the polymer was analyzed by 1H-NMR. The copolymerization compositions of MMA, DM, and HEMA in the polymer were 30 mol %, 10 mol %, and 60 mol %, respectively. The weight average molecular weight (Mw) was 210,000. The polymer solution with a polymer concentration of 0.8 W/V % in ethanol used as a coating solvent was coated to the polyester nonwoven fabric C. The coated amount was 20 mg/m$^2$ per unit area on the entire surface area of the material. In the same way as above, a leukocyte-removing capability test, a pressure test during recovery, a hemolysis test after filtration, and an abnormal prion protein-removing capability test 5 were performed. The leukocyte-removing capability, blood processing pressure, Hemolysis Level, and abnormal prion protein-removing capability were found to be 4.68, 12.0 kPa, 0.3%, and 1.6, respectively.

Example 9

Polymerization, purification, and drying were carried out in the same manner as in Example 1, except for using a monomer charge ratio of MMA 30 mol %, DM 10 mol %, and HEMA 60 mol %. The copolymerization composition of the polymer was analyzed by 1H-NMR. The copolymerization compositions of MMA, DM, and HEMA in the polymer were 30 mol %, 10 mol %, and 60 mol %, respectively. The weight average molecular weight (Mw) was 210,000. The polymer solution with a polymer concentration of 0.8 W/V % in ethanol used as a coating solvent was coated to the polyester nonwoven fabric C. The coated amount was 20 mg/m$^2$ per unit area on the entire surface area of the material. In the same way as above, a leukocyte-removing capability test, a pressure test during recovery, a hemolysis test after filtration, and an abnormal prion protein-removing capability test 5 were performed. The leukocyte-removing capability, blood processing pressure, Hemolysis Level, and abnormal prion protein-removing capability were found to be 5.43, 11.8 kPa, 0.2%, and 1.7, respectively.

Example 10

Polymerization, purification, and drying were carried out in the same manner as in Example 1, except for using a monomer charge ratio of ethyl methacrylate (hereinafter, abbreviated as "EMA") 30 mol %, DM 10 mol %, and HEMA 60 mol %. The copolymerization composition of the polymer was analyzed by 1H-NMR. The copolymerization compositions of EMA, DM, and HEMA in the polymer were 30 mol %, 10 mol %, and 60 mol %, respectively. The weight average molecular weight (Mw) was 220,000. The polymer solution with a polymer concentration of 0.8 W/V % in ethanol used as a coating solvent was coated to the polyester nonwoven fabric C. The coated amount was 19 mg/m$^2$ per unit area on the entire surface area of the material. In the same way as above, a leukocyte-removing capability test, a pressure test during recovery, a hemolysis test after filtration, and an abnormal prion protein-removing capability test 6 were performed. The leukocyte-removing capability, blood processing pressure, Hemolysis Level, and abnormal prion protein-removing capability were found to be 5.22, 10.5 kPa, 0.3%, and 4.1 or more, respectively.

Example 11

Polymerization, purification, and drying were carried out in the same manner as in Example 1, except for using a monomer charge ratio of MMA 30 mol %, diethylaminoethyl methacrylate (hereinafter, abbreviated as "DE") 10 mol %, and HEMA 60 mol %. The copolymerization composition of the polymer was analyzed by 1H-NMR. The copolymerization compositions of EMA, DM, and HEMA in the polymer were 30 mol %, 10 mol %, and 60 mol %, respectively. The weight average molecular weight (Mw) was 200,000. The polymer solution with a polymer concentration of 0.8 W/V % in ethanol used as a coating solvent was coated to the polyester nonwoven fabric C. The coated amount was 20 mg/m$^2$ per unit area on the entire surface area of the material. In the same way as above, a leukocyte-removing capability test, a pressure test during recovery, a hemolysis test after filtration, and an abnormal prion protein-removing capability test 6 were performed. The leukocyte-removing capability, blood processing pressure, Hemolysis Level, and abnormal prion protein-removing capability were found to be 4.58, 12.3 kPa, 0.4%, and 4.1 or more, respectively.

Example 12

Polymerization, purification, and drying were carried out in the same manner as in Example 1, except for using a monomer charge ratio of MMA 30 mol %, DM 10 mol %, and hydroxypropyl methacrylate (hereinafter, abbreviated as "HPMA") 60 mol %. The copolymerization composition of the polymer was analyzed by 1H-NMR. The copolymerization compositions of MMA, DM, and HPMA in the polymer were 30 mol %, 10 mol %, and 60 mol %, respectively. The weight average molecular weight (Mw) was 280,000. The polymer solution with a polymer concentration of 0.8 W/V % in ethanol used as a coating solvent was coated to the polyester nonwoven fabric C. The coated amount was 22 mg/m$^2$ per unit area on the entire surface area of the material. In the same way as above, a leukocyte-removing capability test, a pressure test during recovery, a hemolysis test after filtration, and an abnormal prion protein-removing capability test 6 were performed. The leukocyte-removing capability, blood processing pressure, Hemolysis Level, and abnormal prion protein-removing capability were found to be 4.83, 15.0 kPa, 0.2%, and 4.1 or more, respectively.

Example 13

Polymerization, purification, and drying were carried out in the same manner as in Example 1, except for using a monomer charge ratio of butyl acrylate (hereinafter, abbreviated as "BA") 40 mol % used as the hydrophobic polymerizable monomer, diethylaminoethyl acrylate (hereinafter, abbreviated as "DEA") 10 mol % used as the polymerizable monomer containing a basic nitrogen-containing part, and hydroxybutyl acrylate (hereinafter, abbreviated as "HBA") 50 mol % used as the monomer containing a protonic neutral hydrophilic part. The copolymerization composition of the polymer was analyzed by 1H-NMR. The copolymerization compositions of BA, DEA, and HPA in the polymer were 40 mol %, 10 mol %, and 50 mol %, respectively. The weight average molecular weight (Mw) was 150,000. The polymer solution with a polymer concentration of 0.8 W/V % in ethanol used as a coating solvent was coated to the polyester nonwoven fabric C. The coated amount was 21 mg/m$^2$ per unit area on the entire surface area of the material. In the same way as above, a leukocyte-removing capability test, a pressure test during recovery, a hemolysis test after filtration, and an abnormal prion protein-removing capability test 1 were performed. The leukocyte-removing capability, blood processing pressure, Hemolysis Level, and abnormal prion protein-removing capability were found to be 4.75, 11.5 kPa, 0.3%, and 2.0 or more, respectively.

Comparative Example 1

Polymerization, purification, and drying were carried out in the same manner as in Example 1, except for using a monomer charge ratio of MMA 30 mol %, DM 3 mol %, and HEMA 67 mol %. The copolymerization composition of the polymer was analyzed by 1H-NMR. The copolymerization compositions of MMA, DM, and HEMA in the polymer were 30 mol %, 3 mol %, and 67 mol %, respectively. The weight average molecular weight (Mw) was 200,000. The polymer solution with a polymer concentration of 0.8 W/V % in ethanol used as a coating solvent was coated to the polyester nonwoven fabric C. The coated amount was 19 mg/m$^2$ per unit area on the entire surface area of the material. In the same way as above, a leukocyte-removing capability test, a pressure test during recovery, a hemolysis test after filtration, and an abnormal prion protein-removing capability test 3 were performed. The leukocyte-removing capability, blood processing pressure, Hemolysis Level, and abnormal prion protein-removing capability were found to be 4.88, 10.2 kPa, 0.2%, and 0.5, respectively. In the case where the polymerization composition of the polymerizable monomer containing a basic nitrogen-containing part was less than 5 mol %, adsorption of the abnormal prion protein was reduced, resulting in decreasing the capability of removing the abnormal prion protein.

Comparative Example 2

Polymerization, purification, and drying were carried out in the same manner as in Example 1, except for using a monomer charge ratio of MMA 30 mol %, DM 16 mol %, and HEMA 54 mol %. The copolymerization composition of the polymer was analyzed by 1H-NMR. The copolymerization compositions of MMA, DM, and HEMA in the polymer were 30 mol %, 16 mol %, and 54 mol %, respectively. The weight average molecular weight (Mw) was 190,000. The polymer solution with a polymer concentration of 0.8 W/V % in ethanol used as a coating solvent was coated to the polyester nonwoven fabric C. The coated amount was 21 mg/m$^2$ per unit area on the entire surface area of the material. In the same way as above, a leukocyte-removing capability test, a pressure test during recovery, and a hemolysis test after filtration were performed. The blood processing pressure and Hemolysis Level were found to be 11.8 kPa and 2.3%, respectively. In the case of filtration under a cold condition, hemolysis occurred with an increase in the polymerization composition of the polymerizable monomer containing a basic nitrogen-containing part, and the Hemolysis Level did not meet the standard (0.8%).

Comparative Example 3

Polymerization, purification, and drying were carried out in the same manner as in Example 1, except for using a monomer charge ratio of MMA 15 mol %, DM 10 mol %, and HEMA 75 mol %. The copolymerization composition of the polymer was analyzed by 1H-NMR. The copolymerization compositions of MMA, DM, and HEMA in the polymer were 15 mol %, 10 mol %, and 75 mol %, respectively. The weight average molecular weight (Mw) was 220,000. The polymer solution with a polymer concentration of 0.8 W/V % in ethanol used as a coating solvent was coated to the polyester nonwoven fabric C. The coated amount was 20 mg/m$^2$ per unit area on the entire surface area of the material. In the same way as above, a leukocyte-removing capability test, a pressure test during recovery, a hemolysis test after filtration, and an abnormal prion protein-removing capability test 3 were performed. The leukocyte-removing capability, blood processing pressure, Hemolysis Level, and abnormal prion protein-removing capability were found to be 5.11, 7.8 kPa, 0.3%, and 0.5, respectively.

Comparative Example 4

Polymerization, purification, and drying were carried out in the same manner as in Example 1, except for using a monomer charge ratio of MMA 45 mol %, DM 10 mol %, and HEMA 45 mol %. The copolymerization composition of the polymer was analyzed by 1H-NMR. The copolymerization compositions of MMA, DM, and HEMA in the polymer were 45 mol %, 10 mol %, and 45 mol %, respectively. The weight average molecular weight (Mw) was 180,000. The polymer solution with a polymer concentration of 0.8 W/V % in ethanol used as a coating solvent was coated to the polyester nonwoven fabric C. The coated amount was 22 mg/m$^2$ per unit area on the entire surface area of the material. In the same way as above, a leukocyte-removing capability test, a pressure test during recovery, and a hemolysis test after filtration were performed. However, the test was stopped because of low flowability of the blood product, high blood processing pressure (more than 60 kPa), and a fear of breakage of the tube and syringe, so it was impossible to measure the leukocyte-removing capability and hemolysis.

Comparative Example 5

Polymerization, purification, and drying were carried out in the same manner as in Example 1, except for using a monomer charge ratio of DM 3 mol % and HEMA 97 mol %. The copolymerization composition of the polymer was analyzed by 1H-NMR. The copolymerization compositions of DM and HEMA in the polymer were 3 mol % and 97 mol %, respectively. The weight average molecular weight (Mw) was 550,000. The polymer solution with a polymer concentration of 0.8 W/V % in ethanol used as a coating solvent was coated to a polyester nonwoven fabric C with a specific surface area of 1.47 m$^2$/g, average fiber diameter of 1.2 μM, and weight per unit area of 40 g/m$^2$. The coated amount was 7 mg/m$^2$ per unit area on the entire surface area of the material. In the same way as above, a leukocyte-removing capability test, a pressure test during recovery, a hemolysis test after filtration, and an abnormal prion protein-removing capability test 2 were performed. The leukocyte-removing capability, blood processing pressure, Hemolysis Level, and abnormal prion protein-removing capability were found to be 4.92, 6.8 kPa, 0.2%, and 0.2, respectively.

Comparative Example 6

A polyester nonwoven fabric C with a specific surface area of 1.47 m$^2$/g, average fiber diameter of 1.2 μm, and weight per unit area of 40 g/m$^2$ was used without coating with a polymer. In the same way as above, a leukocyte-removing capability test, a pressure test during recovery, a hemolysis test after filtration, and an abnormal prion protein-removing capability test 2 were performed. The leukocyte-removing capability, blood processing pressure, Hemolysis Level, and abnormal prion protein-removing capability were found to be 4.55, 20.3 kPa, 0.2%, and 0.0, respectively.

Comparative Example 7

Methacrylic acid having a carboxyl group (hereinafter, abbreviated as "MAA") was used as an acidic monomer.
Polymerization, purification, and drying were carried out in the same manner as in Example 1, except for using a monomer charge ratio of MMA 30 mol %, MAA 10 mol %, and HEMA 60 mol %. The copolymerization composition of the polymer was analyzed by 1H-NMR. The copolymerization compositions of MMA, MAA, and HEMA in the polymer were 30 mol %, 10 mol %, and 60 mol %, respectively. The weight average molecular weight (Mw) was 230,000. The polymer solution with a polymer concentration of 0.8 W/V % in ethanol used as a coating solvent was coated to the polyester nonwoven fabric C. The coated amount was 22 mg/m$^2$ per unit area on the entire surface area of the material. In the same way as above, a leukocyte-removing capability test, a pressure test during recovery, a hemolysis test after filtration, and an abnormal prion protein-removing capability test 3 were performed. The leukocyte-removing capability, blood processing pressure, Hemolysis Level, and abnormal prion protein-removing capability were found to be 5.36, 10.0 kPa, 0.4%, and 0.0, respectively. The polymer having an acidic monomer was found to have no capability to remove an abnormal prion protein.

Comparative Example 8

Polymerization, purification, and drying were carried out in the same manner as in Example 1, except for using a monomer charge ratio of DM 10 mol % and HEMA 90 mol %. The copolymerization composition of the polymer was analyzed by 1H-NMR. The copolymerization compositions of DM and HEMA in the polymer were 10 mol % and 90 mol %, respectively. The weight average molecular weight (Mw) was 500, 000. The polymer solution with a polymer concentration of 0.8 W/V % in ethanol used as a coating solvent was coated to a polyester nonwoven fabric C with a specific surface area of 1.47 m$^2$/g, average fiber diameter of 1.2 μm, and weight per unit area of 40 g/m$^2$ as a material. The coated amount was 18 mg/m$^2$ per unit area on the entire surface area of the material. In the same way as above, a leukocyte-removing capability test, a pressure test during recovery, a hemolysis test after filtration, and an abnormal prion protein-removing capability test 3 were performed. The leukocyte-removing capability, blood processing pressure, Hemolysis Level, and abnormal prion protein-removing capability were found to be 3.75, 15.0 kPa, 0.3%, and 0.5, respectively.

Comparative Example 9

Polymerization, purification, and drying were carried out in the same manner as in Example 1, except for using a monomer charge ratio of MMA 90 mol % and DM 10 mol %. The copolymerization composition of the polymer was analyzed by 1H-NMR. The copolymerization compositions of MMA and DM in the polymer were 90 mol % and 10 mol %, respectively. The weight average molecular weight (Mw) was 240,000. The polymer solution with a polymer concentration of 0.8 W/V % in ethanol used as a coating solvent was coated to a polyester nonwoven fabric C with a specific surface area of 1.47 m$^2$/g, average fiber diameter of 1.2 μm, and weight per unit area of 40 g/m$^2$ as a material as a material. The coated amount was 21 mg/m$^2$ per unit area on the entire surface area of the material. In the same way as above, a leukocyte-removing capability test, a pressure test during recovery, and a hemolysis test after filtration were performed. However, the test was stopped because of low flowability of the blood product, high blood processing pressure (more than 60 kPa), and a fear of breakage of the tube and syringe, so it was impossible to measure the leukocyte-removing capability and hemolysis.

Comparative Example 10

The abnormal prion protein-removing capability test 4 was performed using a commercially-available leukocyte removal filter for whole blood product (WBF2, manufactured by Pall), and the abnormal prion protein-removing capability was found to be 0.4.

Table 1 shows the results of Examples and Comparative Examples. In Table 1, the electron beam sterilization and autoclave sterilization were abbreviated as E.B. and A.C., respectively.

TABLE 1

| | Hydrophobic | | Basic | | Hydrophilic | | Acidic | | | Prion | Leukocyte- | Blood processing | Hemolysis |
|---|---|---|---|---|---|---|---|---|---|---|---|---|---|
| | mol % | Monomer | mol % | Monomer | mol % | Monomer | mol % | Monomer | Sterilization method | removing capability | Removing Capability | pressure (kPa) | Level (%) |
| Example 1 | 20 | MMA | 5 | DM | 75 | HEMA | 0 | — | γ-ray | >2.0 | 4.12 | 9.8 | 0.2 |
| Example 2 | 20 | | 13 | | 67 | | 0 | — | γ-ray | >2.0 | 5.68 | 8.1 | 0.5 |
| Example 3 | 30 | | 10 | | 60 | | 0 | — | γ-ray | 3.8 | 5.68 | 11.4 | 0.4 |
| Example 4 | 40 | | 5 | | 55 | | 0 | — | γ-ray | >2.0 | 5.17 | 12.5 | 0.3 |
| Example 5 | 40 | | 13 | | 47 | | 0 | — | γ-ray | 2.4 | 5.68 | 10.9 | 0.5 |
| Example 6 | 30 | | 10 | | 60 | | 0 | — | A.C. | 1.5 | 5.86 | 13.2 | 0.4 |
| Example 7 | 30 | | 10 | | 60 | | 0 | — | A.C. | 1.2 | 5.12 | 11.5 | 0.3 |
| Example 8 | 30 | | 10 | | 60 | | 0 | — | E.B. | 1.6 | 4.68 | 12.0 | 0.3 |
| Example 9 | 30 | | 10 | | 60 | | 0 | — | E.B. + A.C. | 1.7 | 5.43 | 11.8 | 0.2 |
| Example 10 | 30 | EMA | 10 | | 60 | | 0 | — | A.C. | >4.1 | 5.22 | 10.5 | 0.3 |
| Example 11 | 30 | MMA | 10 | DE | 60 | | 0 | — | γ-ray | >4.1 | 4.58 | 12.3 | 0.4 |
| Example 12 | 30 | | 10 | DM | 60 | HPMA | 0 | — | E.B. | >4.1 | 4.83 | 15.0 | 0.2 |
| Example 13 | 40 | BA | 10 | DEA | 50 | HBA | 0 | — | A.C. | >2.0 | 4.75 | 11.5 | 0.3 |
| Comp Ex 1 | 30 | MMA | 3 | DM | 67 | HEMA | 0 | — | γ-ray | 0.5 | 4.88 | 10.2 | 0.2 |
| Comp Ex 2 | 30 | | 16 | | 54 | | 0 | — | γ-ray | — | — | 11.8 | 2.3 |
| Comp Ex 3 | 15 | | 10 | | 75 | | 0 | — | γ-ray | 0.5 | 5.11 | 7.8 | 0.3 |
| Comp Ex 4 | 45 | | 10 | | 45 | | 0 | — | γ-ray | — | — | >60 | — |
| Comp Ex 5 | 0 | — | 3 | | 87 | | 0 | — | γ-ray | 0.2 | 4.92 | 6.8 | 0.2 |
| Comp Ex 6 | 0 | — | 0 | — | 0 | — | 0 | — | γ-ray | 0 | 4.55 | 20.3 | 0.2 |
| Comp Ex 7 | 30 | MMA | 0 | — | 60 | HEMA | 10 | MAA | γ-ray | 0 | 5.36 | 10.0 | 0.4 |
| Comp Ex 8 | 0 | — | 10 | DM | 90 | | 0 | — | γ-ray | 0.5 | 3.75 | 15.0 | 0.3 |
| Comp Ex 9 | 90 | MMA | 10 | | 0 | | 0 | — | γ-ray | — | — | >60 | — |
| Comp Ex 10 | | | | | | | | | | 0.4 | | | |

INDUSTRIAL APPLICABILITY

The method of removing an abnormal prion protein from a blood product according to the present invention is useful for preventing transfusion-transmission of transmissible spongiform encephalopathy (TSE) caused by an abnormal prion protein in transfusion clinical field and for preventing transfusion side effects caused by leukocytes.

The invention claimed is:
1. A method of removing an abnormal prion protein from a blood product, comprising: filtering a blood product which contains an abnormal prion protein through a filter packed with a carrier coated with a polymer, which is formed of three units including 20 mol % or more and 40 mol % or less of a unit originating from a hydrophobic polymerizable monomer, 5 mol % or more and 13 mol % or less of a unit originating from a polymerizable monomer containing a basic nitrogen-containing part, and a unit originating from a polymerizable monomer containing a protonic neutral hydrophilic part as the balance; and recovering the filtered blood product,
 wherein the blood product is an erythrocyte product or plasma product; and
 wherein the abnormal prion protein-removing capability of the method is 2.0 or higher, the abnormal prion protein-removing capability being determined by subtracting the titer of abnormal prion protein of Supplemented Postfiltration Blood from the titer of abnormal prion protein of Supplemented Prefiltration Blood.

2. A method of removing an abnormal prion protein from a blood product according to claim 1, wherein the filter is subjected to radiation sterilization and then autoclave sterilization.

3. A method of removing an abnormal prion protein from a blood product according to claim 2, wherein the radiation is γ-rays or electron beams.

4. A method of removing an abnormal prion protein from a blood product according to claim 1, wherein the polymer is a vinyl-type polymer.

5. A method of removing an abnormal prion protein from a blood product according to claim 1, wherein the hydrophobic polymerizable monomer, polymerizable monomer containing a basic nitrogen-containing part, and polymerizable monomer containing a protonic neutral hydrophilic part are acrylic acid derivatives and/or methacrylic acid derivatives.

6. A method of removing an abnormal prion protein from a blood product according to claim 1, wherein the basic nitrogen-containing part is a tertiary amino group.

7. A method of removing an abnormal prion protein from a blood product according to claim 1, wherein the protonic neutral hydrophilic part is a hydroxyl group.

8. A method of removing an abnormal prion protein from a blood product according to claim 1, wherein the filter is a leukocyte removal filter.

9. A method of removing an abnormal prion protein from a blood product according to claim 8, wherein the carrier coated with the polymer is a fibrous medium or a sponge-like structural material.

10. A method of removing an abnormal prion protein from a blood product according to claim 8, wherein a specific surface area of the carrier coated with the polymer is $1.0 \text{ m}^2/\text{g}$ or more and $5.0 \text{ m}^2/\text{g}$ or less.

11. A method of removing an abnormal prion protein from a blood product according to claim 8, wherein an average pore diameter of the carrier coated with the polymer is 1 μm or more and 60 μm or less.

12. A method of removing an abnormal prion protein from a blood product according to claim 8, wherein a filling density of the carrier coated with the polymer is $0.1 \text{ g/cm}^3$ or more and $0.5 \text{ g/cm}^3$ or less.

13. A method of removing an abnormal prion protein from a blood product according to claim 8, wherein porosity of the carrier coated with the polymer is 60% or more and 90% or less.

14. A method of removing an abnormal prion protein from a blood product according to claim 8, wherein the carrier coated with the polymer is a nonwoven fabric.

15. A method of removing an abnormal prion protein from a blood product according to claim 14, wherein a fiber diameter of the nonwoven fabric is 0.3 μm or more and 3.0 μm or less.

16. A method of removing an abnormal prion protein from a blood product according to claim 1, wherein the prion protein binds to the carrier coated with the polymer.

17. A method of removing an abnormal prion protein from a blood product, comprising: filtering a blood product which contains an abnormal prion protein through a filter packed with a carrier coated with a polymer, which is formed of three units including 27 mol % or more and 33 mol % or less of a unit originating from a hydrophobic polymerizable monomer, 8 mol % or more and 11 mol % or less of a unit originating from a polymerizable monomer containing a basic nitrogen-containing part, and a unit originating from a polymerizable monomer containing a protonic neutral hydrophilic part as the balance; and recovering the filtered blood product, wherein the blood product is an erythrocyte product or plasma product, and wherein the abnormal prion protein-removing capability of the method is 2.0 or higher, the abnormal prion protein-removing capability being determined by subtracting the titer of abnormal prion protein of Supplemented Postfiltration Blood from the titer of abnormal prion protein of Supplemented Prefiltration Blood.

* * * * *